US005953727A

United States Patent [19]
Maslyn et al.

[11] Patent Number: 5,953,727
[45] Date of Patent: Sep. 14, 1999

[54] PROJECT-BASED FULL-LENGTH BIOMOLECULAR SEQUENCE DATABASE

[75] Inventors: Timothy J. Maslyn, Cupertino; Janice Au-Young, Berkeley; Jennifer L. Hillman, San Jose; Harold Hibbert, Fremont; Ingrid E. Akerblom, Redwood City; Rachel J. Cheng, Los Altos; Yuanhua T. Tang, Sunnyvale, all of Calif.

[73] Assignee: Incyte Pharmaceuticals, Inc., Palo Alto, Calif.

[21] Appl. No.: 08/811,758

[22] Filed: Mar. 6, 1997

Related U.S. Application Data

[60] Provisional application No. 60/032,563, Dec. 12, 1996, and provisional application No. 60/028,284, Oct. 10, 1996.

[51] Int. Cl.$^6$ ................................................ G06F 17/30
[52] U.S. Cl. ........................... 707/104; 707/10; 435/6
[58] Field of Search .......................... 707/10, 104; 435/6

[56] References Cited

U.S. PATENT DOCUMENTS 5,523,208  6/1996  Kohler et al. ............................. 435/6
5,706,498  1/1998  Fujiymiya et al. ......................... 707/6

OTHER PUBLICATIONS

Keele, J.W., "A Conceptual Database Model for Genomic Research", Journal of Computational Biology, vol. 1, No. 1, pp. 65–76, 1994.

Matsubara K,. Identification of new genes by systematic analysis of cDNAs and database construction, Current Opinion in Biology, vol. 4, pp. 672–677, 1993.

Fickett, J. W. "Finding genes by computer: the state of the art" TIG vol. 12, No. 8, pp. 316–320, Sep. 1996.

"GDB 6.0 Goals", http://gbd.gdbnet.ad.jp/gdb/docs/gdb6–goals.htm pp. 1–5 Mar. 1995.

The Institute for Genomic Research, TIGR Database. Internet—http://www.tigr.org (Downloaded Dec. 23, 1997).

National Center for Biotechnology Information (Index). Internet—http://www3.ncbi.nlm.nih.gov/ (Downloaded Dec. 23, 1997).

National Center for Biotechnology Information; ENTREZ. Internet—http://www3.ncbi.nlm.nih.gov/entrez (Downloaded Dec. 23, 1997).

National Center for Biotechnology Information; UniGene. Internet—http://www3.ncbi.nlm.nih.gov/unigene (Downloaded Dec. 23, 1997).

National Center for Biotechnology Information; GenBank. Internet—http://www3.ncbi.nlm.nih.gov/web/genbank (Downloaded Dec. 23, 1997).

MAGPIE; Automated Genome Project Investigation Environment. Internet—http://www.mcs.anl.gov/home/gaasterl/magpie.html. (Downloaded Dec. 23, 1997).

Stanford University, Stanford Genomic Resources. Internet—http://genome–www.stanford.edu Sep. 22, 1996 and Dec. 20, 1997.

(List continued on next page.)

Primary Examiner—Jack M. Choules
Attorney, Agent, or Firm—Beyer & Weaver, LLP

[57] ABSTRACT

Disclosed is a relational database system for storing biomolecular sequence information in a manner that allows sequences to be catalogued and searched according to association with one or more projects for obtaining full-length biomolecular sequences from shorter sequences. The relational database has sequence records containing information identifying one or more projects to which each of the sequence records belong. Each project groups together one or more biomolecular sequences generated during work to obtain a full-length gene sequence from a shorter sequence. The computer system has a user interface allowing a user to selectively view information regarding one or more projects. The relational database also provides interfaces and methods for accessing and manipulating and analyzing project-based information.

52 Claims, 20 Drawing Sheets

OTHER PUBLICATIONS

Incyte Pharmaceuticals, LIFESEQ Version 4.2 Release Notes and Physical Data Model, Oct. 1996.

Incyte Pharmaceuticals, LIFESEQ Version 4.1 Release Notes and Physical Data Model, Jul. 1996.

Incyte Pharmaceuticals, LIFESEQ Version 3.4 Release Notes, Jan. 1996.

Incyte Pharmaceuticals, LIFESEQ Verison 2.5 Release Notes, Jun. 1995.

Incyte Pharmaceuticals, LIFESEQ Version 3.0 Release Notes, Sep. 1995.

Incyte Pharmaceuticals, LIFESEQ Verison 4.0 Release Notes, Apr. 1996.

Incyte Pharmaceuticals, *Introduction to the LIFESEQ Database,* Version 3.4, Jan. 1996.

Incyte Pharmaceuticals, *LIFESEQ Training Manual,* Version 4.1, Jul. 1996.

Green, et al., "Ancient Conserved Regions in New Gene Sequences and the Protein Databases", *Science,* v. 259, n. 5102, pp. 1711–1716 (1993).

http://wehih.edu.au/ (1995).

Waldrop, et al., "On–line Archives Let Biologists Interrogate the Genome", *Science,* v. 269, n. 5229, pp. 1356–1358 (1995).

No Author, "Incyte Serves Up Information, part I", *In Vivo the Business & Medicine Report,* p. 32, ISSN: 0258–851X (1996).

Martin, et al., "Accessing Genetics Databases", *Database,* v. 17, n. 1, p. 51(8).

Kanehisa, M. "Toward Pathway Engineering: A New Database Old Genetic and Molecular Pathways." Science and Technology Japan, 1995, No. 59, pp. 34–38.

Gaasterland, T. and Sensen, C. "Using Multiple Tools for Automated Genome Interpretation in an Integrated Environment", Trends In Genetics, Jan. 1996.

Adams, M.D. et al. "Complementary DNA Sequencing: Expressed Sequence Tags and Human Genome Project", Science, Jun. 21, 1991, vol. 252, pp. 1651–1656.

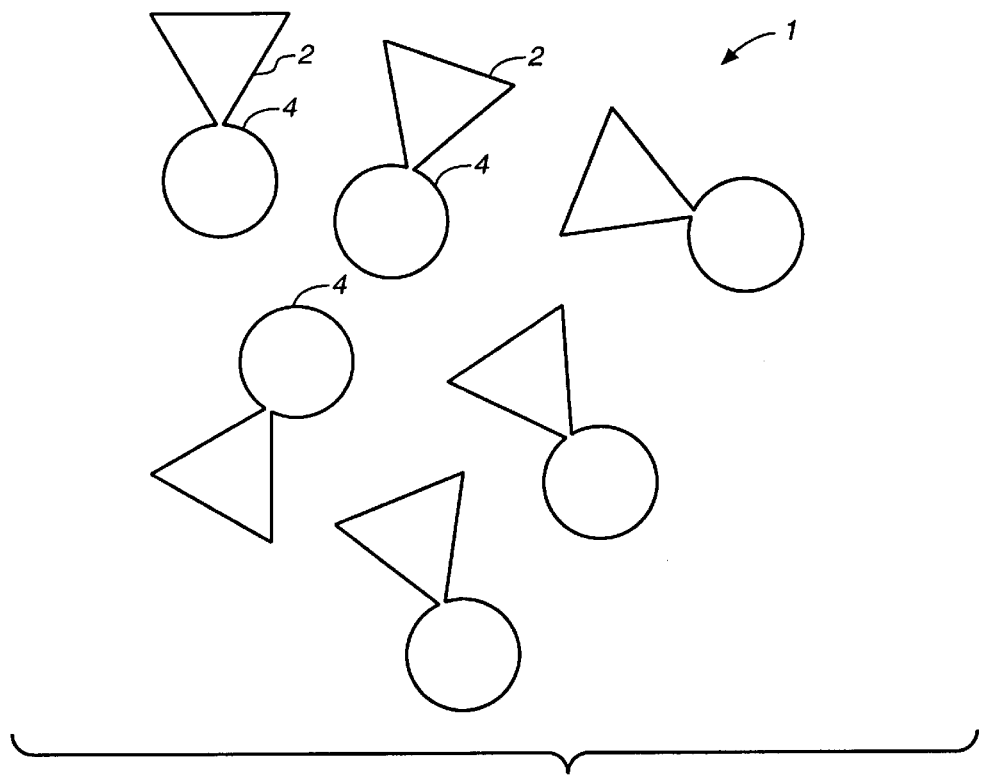
FIG._1A
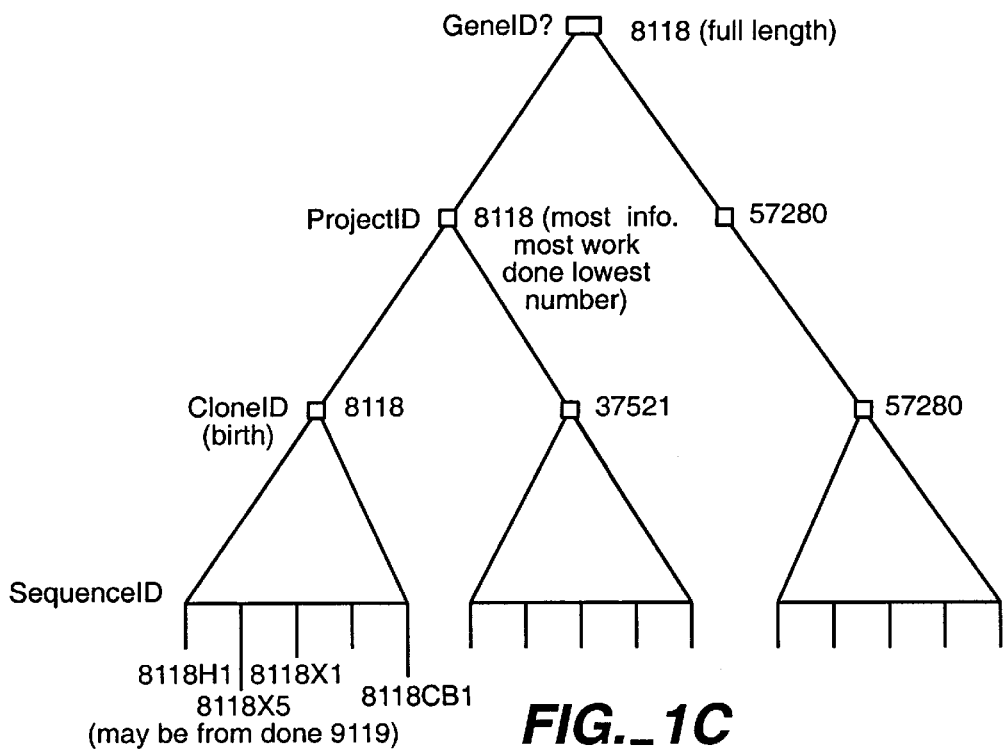
FIG._1C

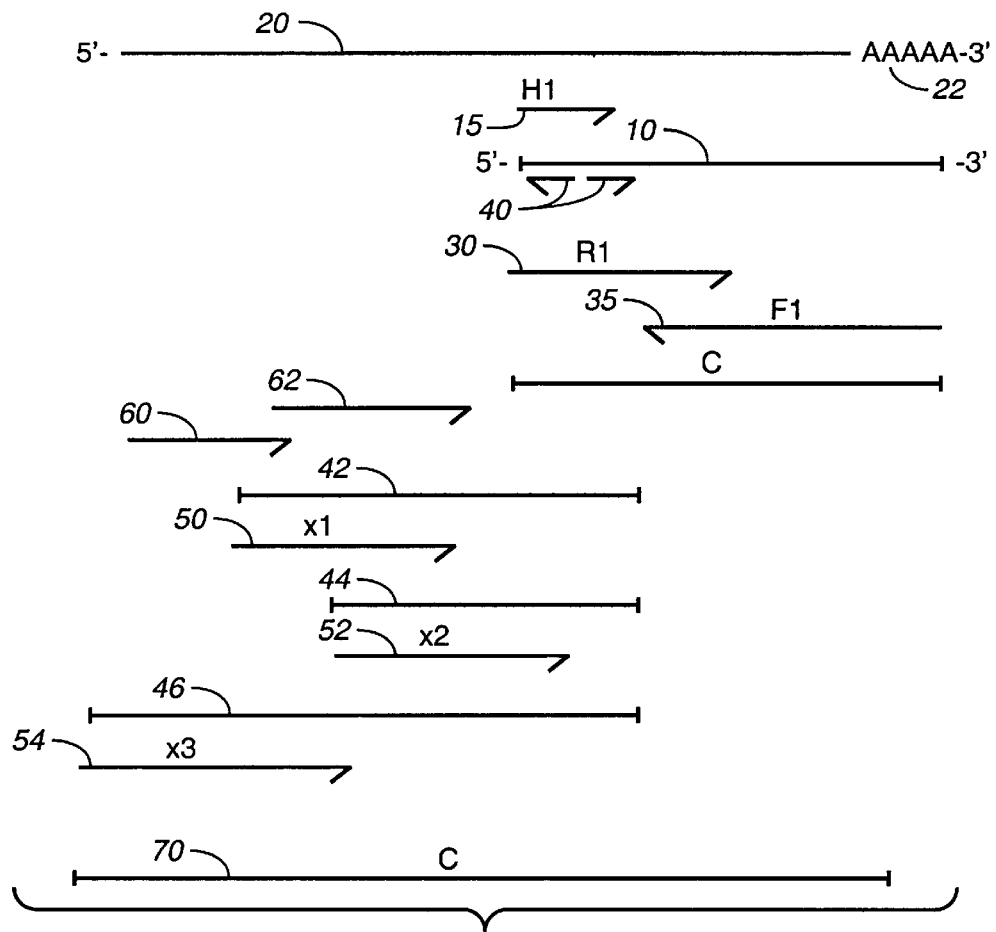
FIG._1B
FIG._1D

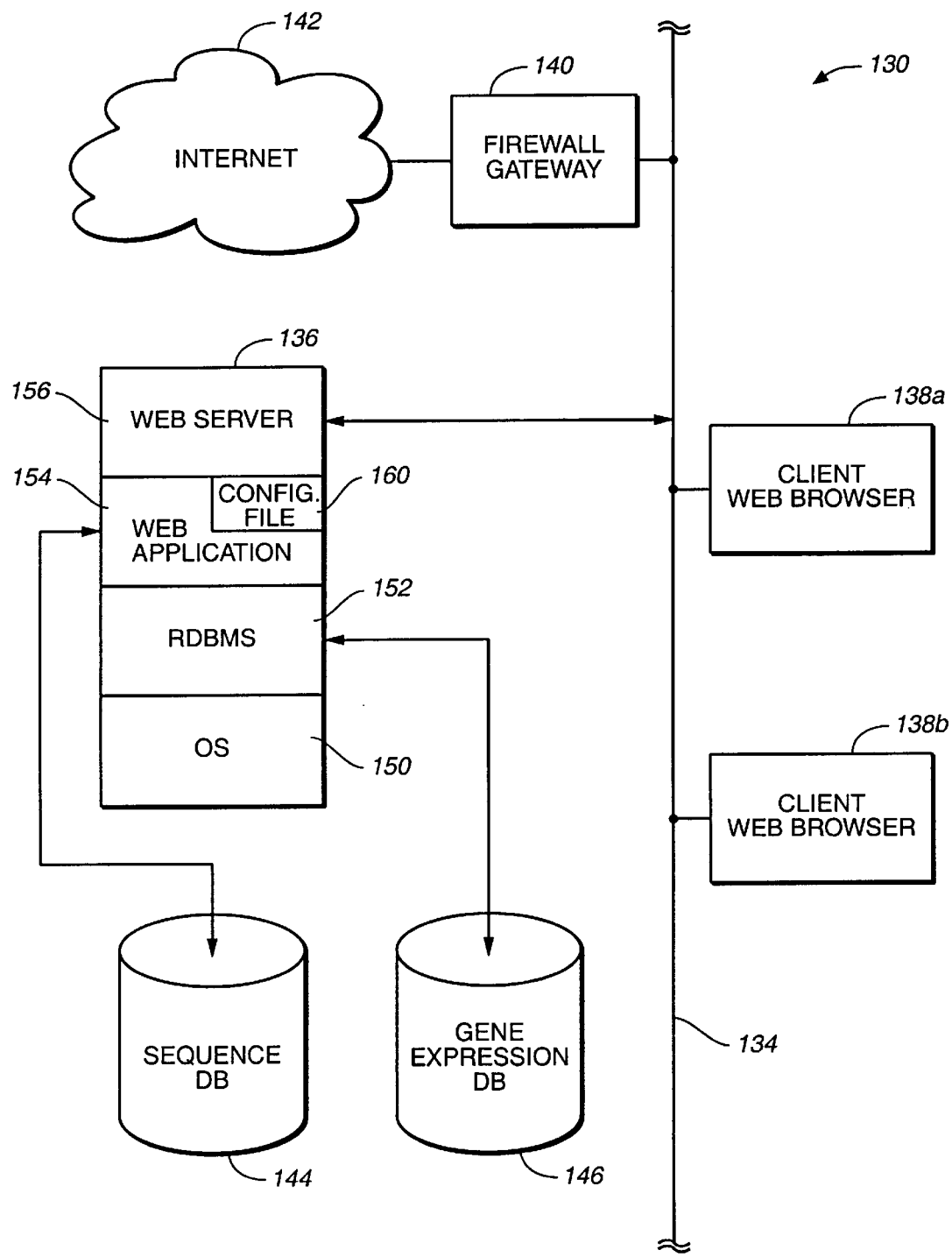
FIG._2A

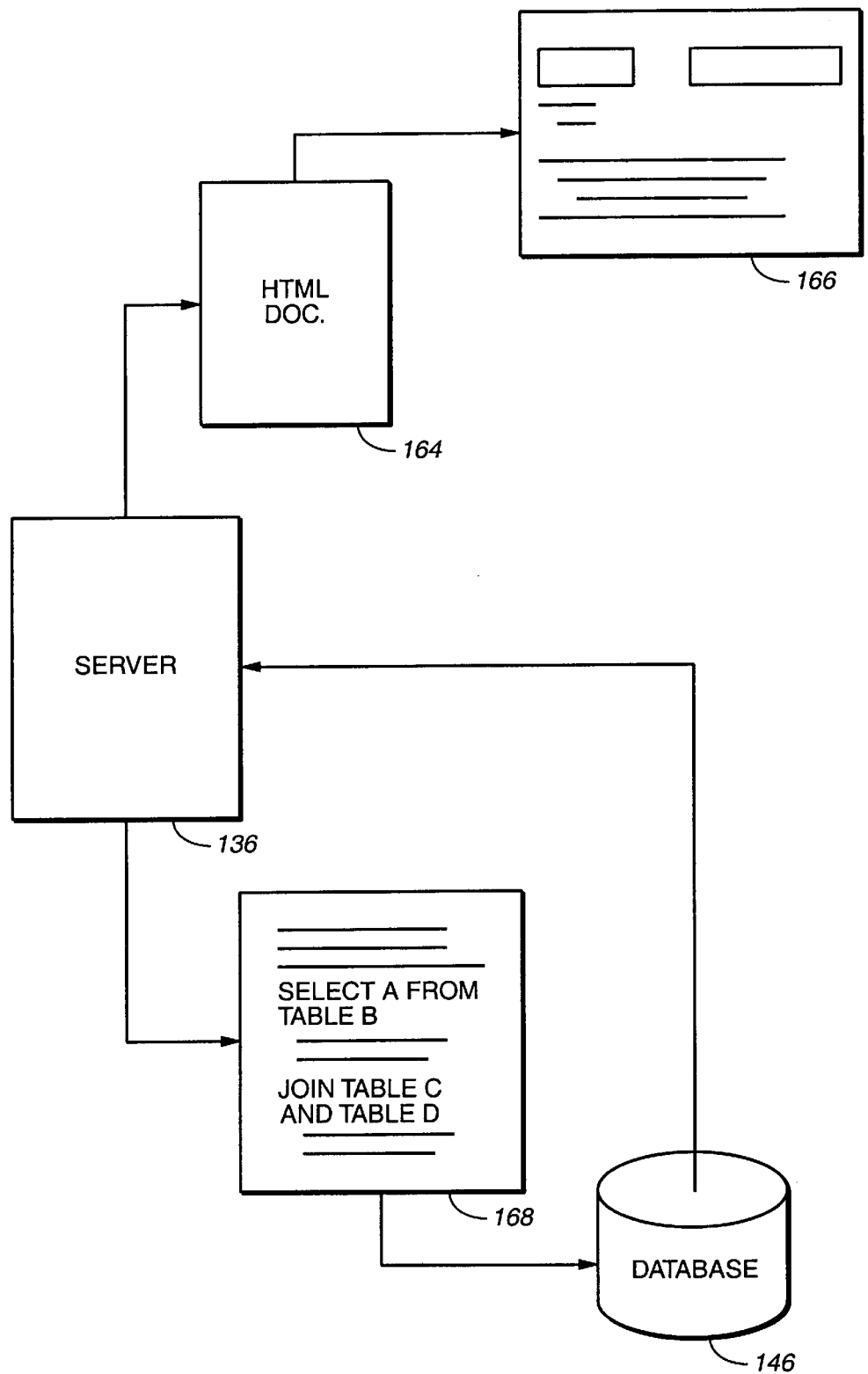
FIG._2B

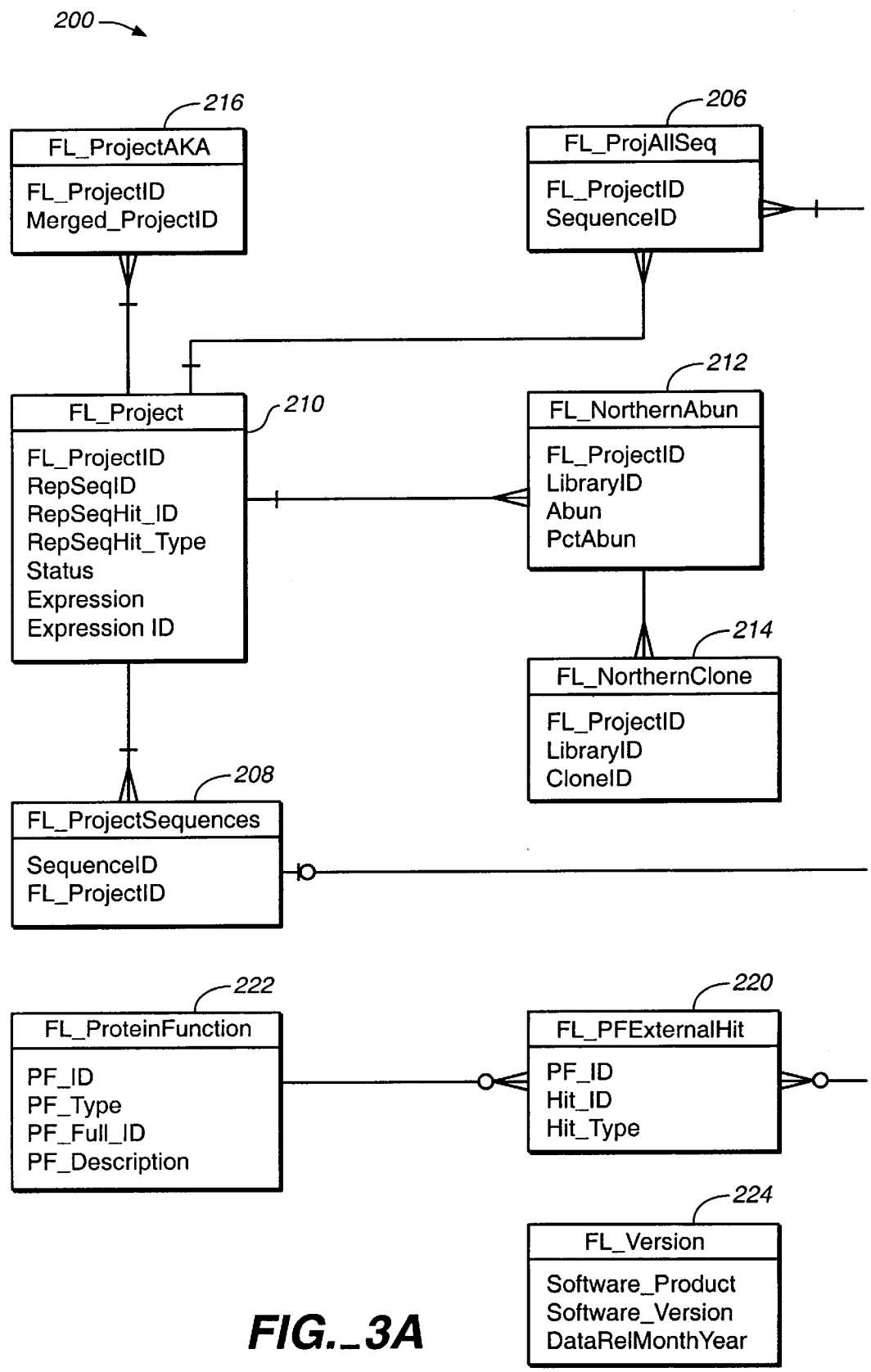
FIG._3A

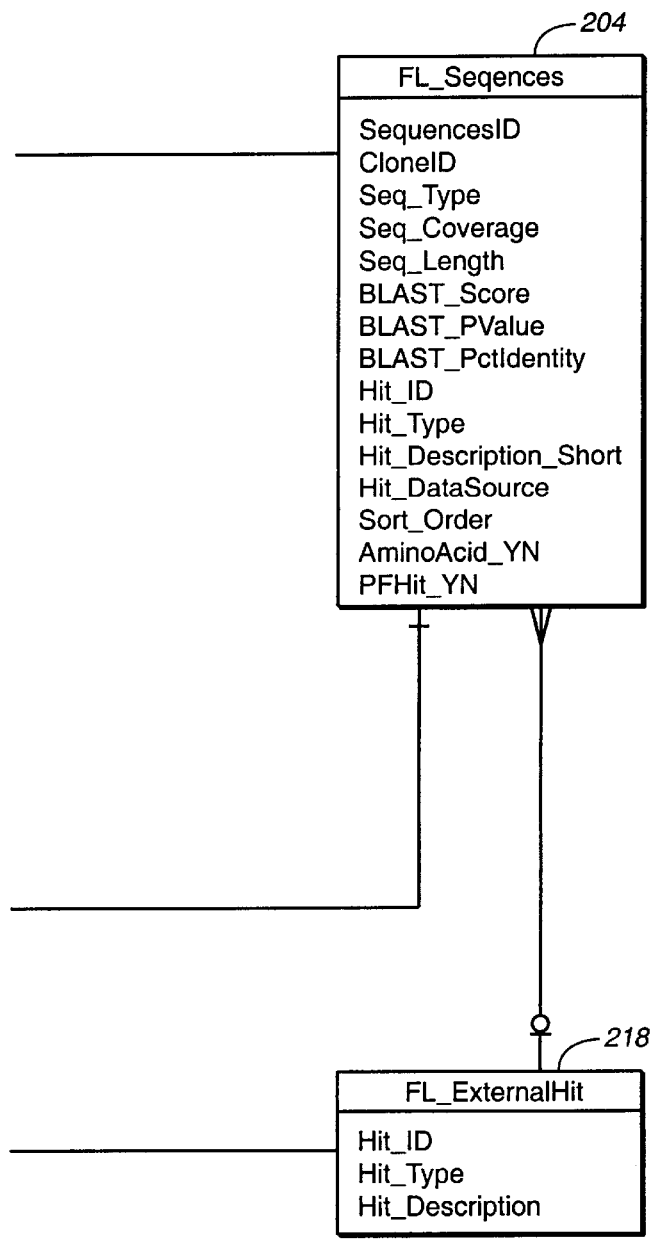
FIG._3B
FIG._3

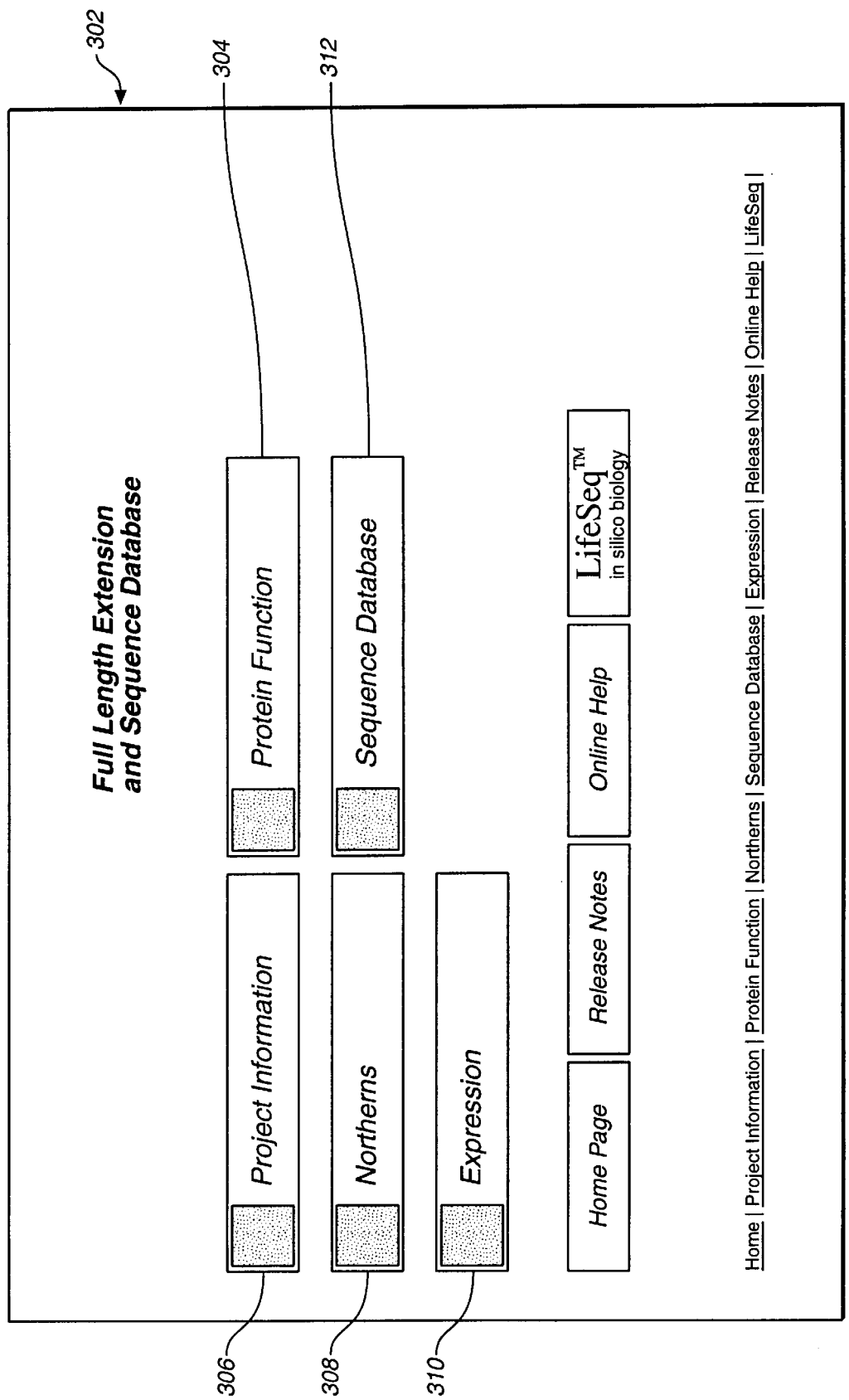
FIG._4

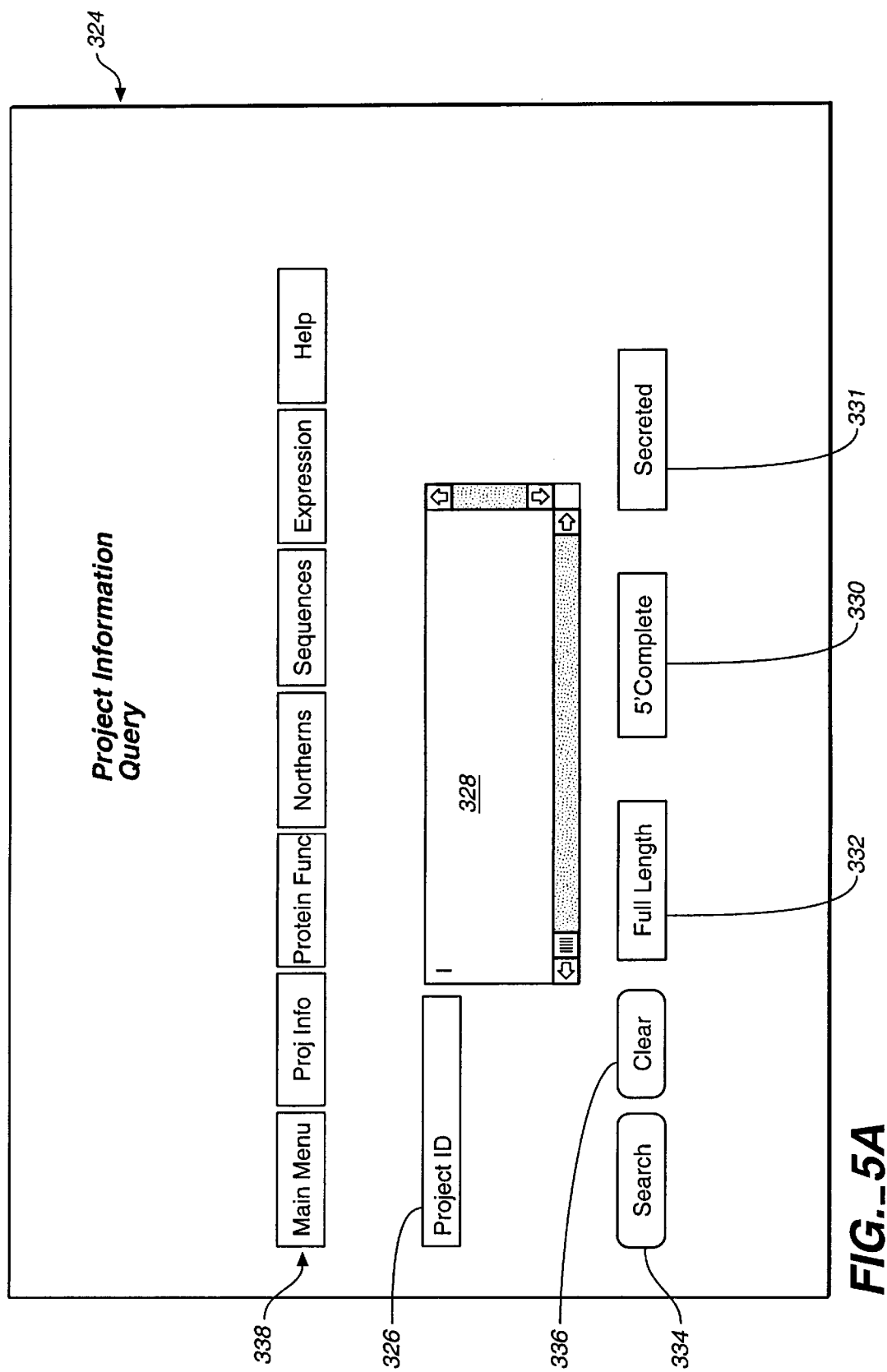
FIG._5A

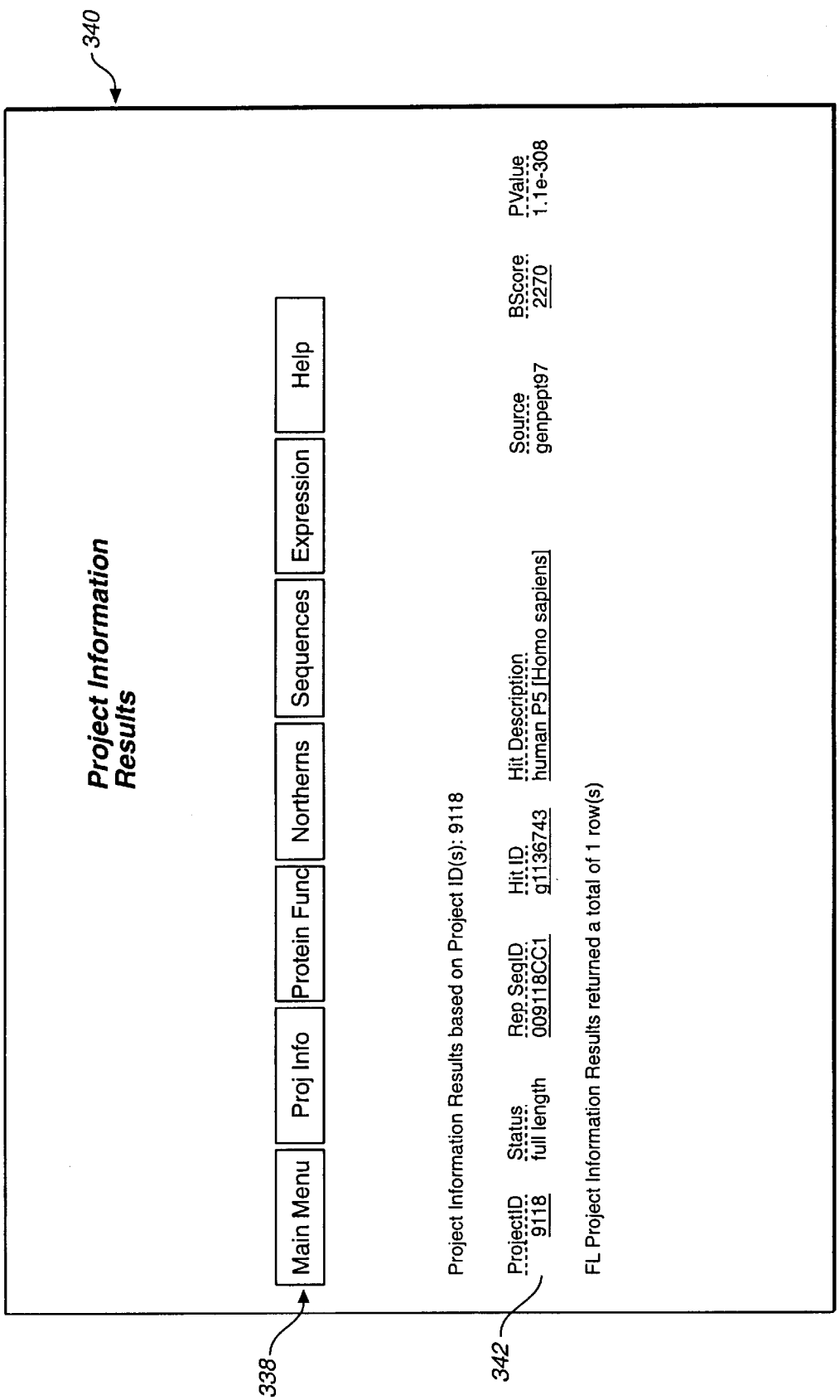
FIG._5B

Sequence Information Results

| Main Menu | Proj Info | Protein Func | Northerns | Sequences | Expression | Help |

Sequence Information Results based on project ID(s):
9118
for sequences clustered with the projects(s)

| Asn | SequenceID | Sequence Type | ProjectID | HitID | Hit Description | 5' Coverage | Source | Score | PValue |
|---|---|---|---|---|---|---|---|---|---|
| ☒ | 009118CC1 | Full length | 9118 | g1136743 | human P5 [Homo sapiens] | | genpept97 | 2270 | 1.1e-308 |
| ☒ | 009118F1 | HTP forward long read | 9118 | g1136743 | human P5 [Homo sapiens] | | genpept97 | 732 | 1.3e-127 |
| ☒ | 009118X3 | HTP extension | 9118 | g1136743 | human P5 [Homo sapiens] | | genpept97 | 691 | 1.4e-108 |
| ☒ | 009118H1 | HTP first pass | 9118 | g1136743 | human P5 [Homo sapiens] | | genpept97 | 469 | 1.4e-61 |
| ☒ | 011255H1 | HTP first pass | 9118 | g1136742 | Human mRNA for protein disulfide isomera | | gb97pri | 827 | 9.4e-98 |
| ☒ | 030811H1 | HTP first pass | 9118 | g1136742 | Human mRNA for protein disulfide isomera | | gb97pri | 1361 | 3.7e-107 |
| ☒ | 031754H1 | HTP first pass | 9118 | g1136742 | Human mRNA for protein disulfide isomera | | gb97pri | 1337 | 7.9e-103 |
| ☒ | 032811H1 | HTP first pass | 9118 | g1136742 | Human mRNA for protein disulfide isomera | | gb97pri | 1327 | 4.5e-106 |
| ☒ | 034208H1 | HTP first pass | 9118 | g1136742 | Human mRNA for protein disulfide isomera | | gb97pri | 1462 | 3.0e-113 |
| ☒ | 043333H1 | HTP first pass | 9118 | g1136742 | Human mRNA for protein disulfide isomera | | gb97pri | 1274 | 1.4e-97 |
| ☒ | 043866H1 | HTP first pass | 9118 | g1136742 | Human mRNA for protein disulfide isomera | | gb97pri | 1468 | 9.4e-114 |
| ☒ | 045238H1 | HTP first pass | 9118 | g1136742 | Human mRNA for protein disulfide isomera | | gb97pri | 975 | 2.8e-94 |

FIG._5C

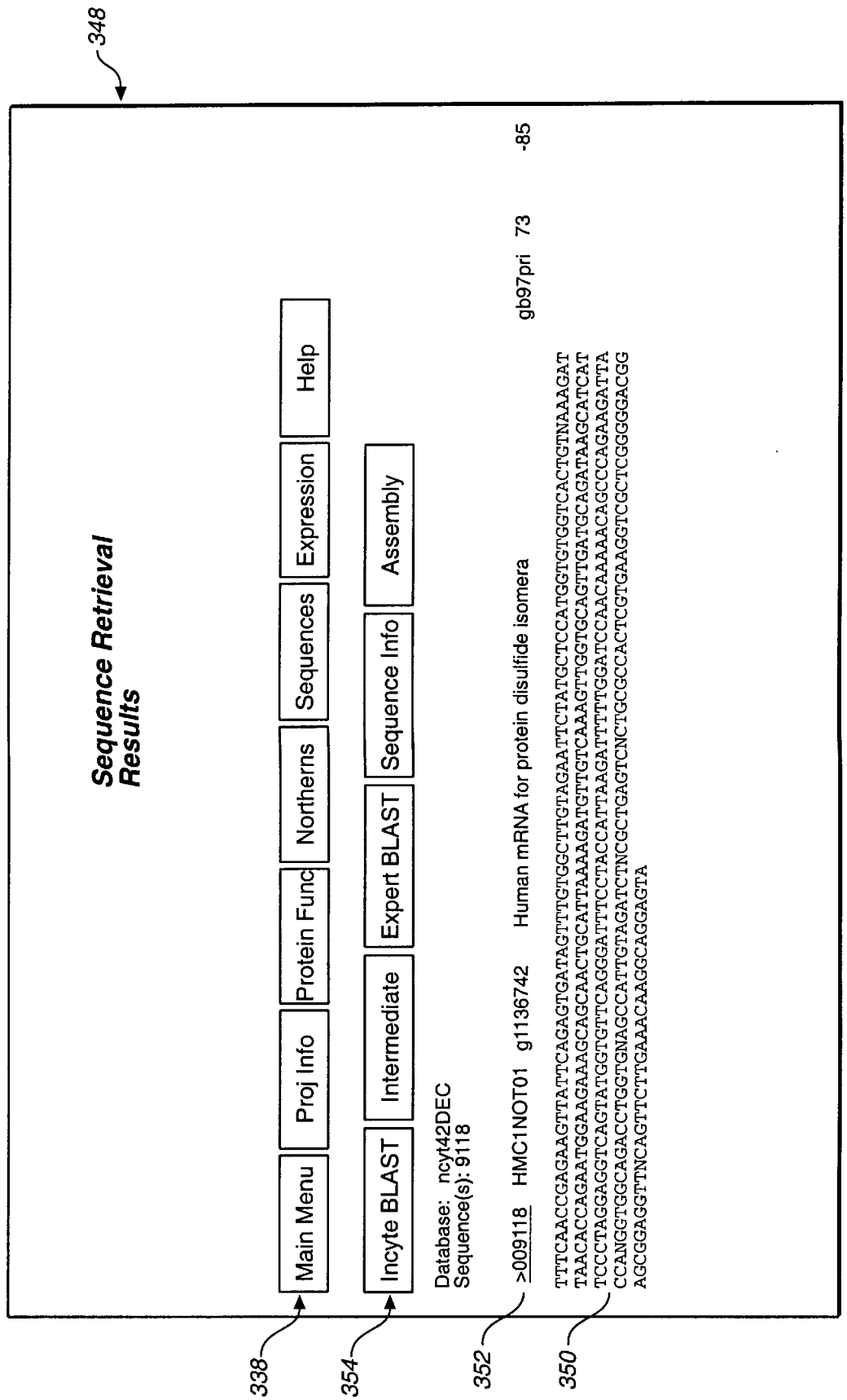
FIG._5D

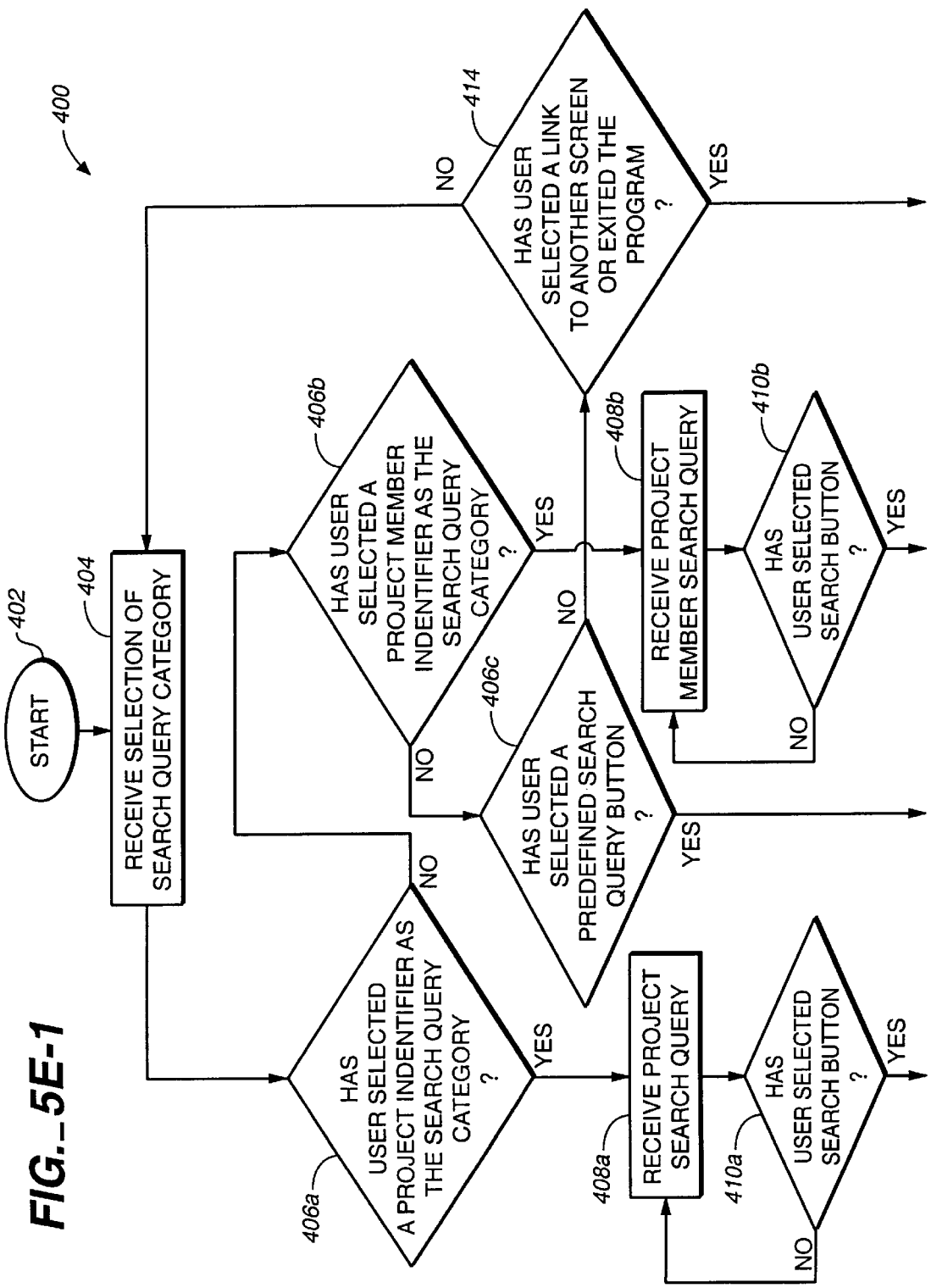
FIG._5E-1

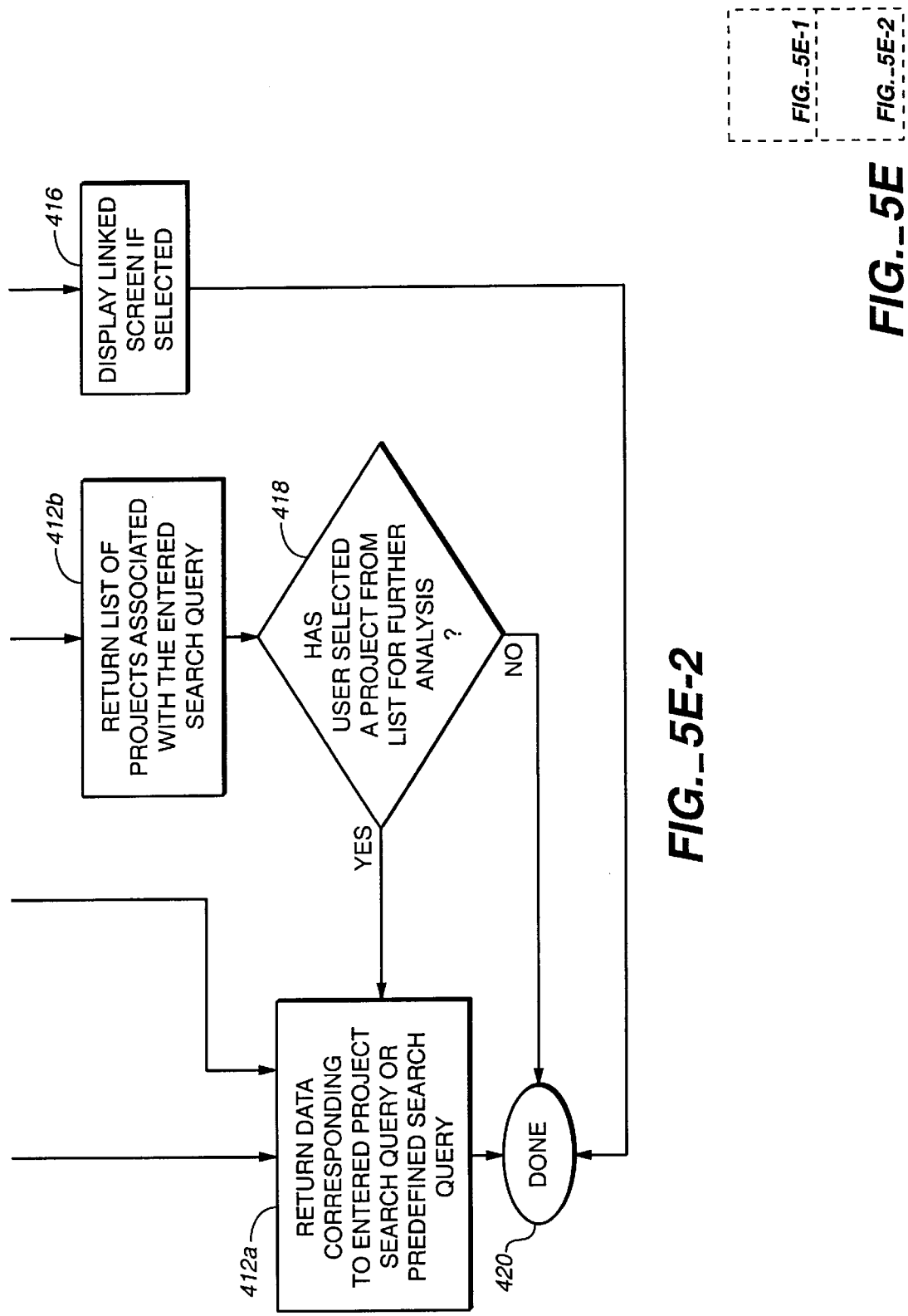

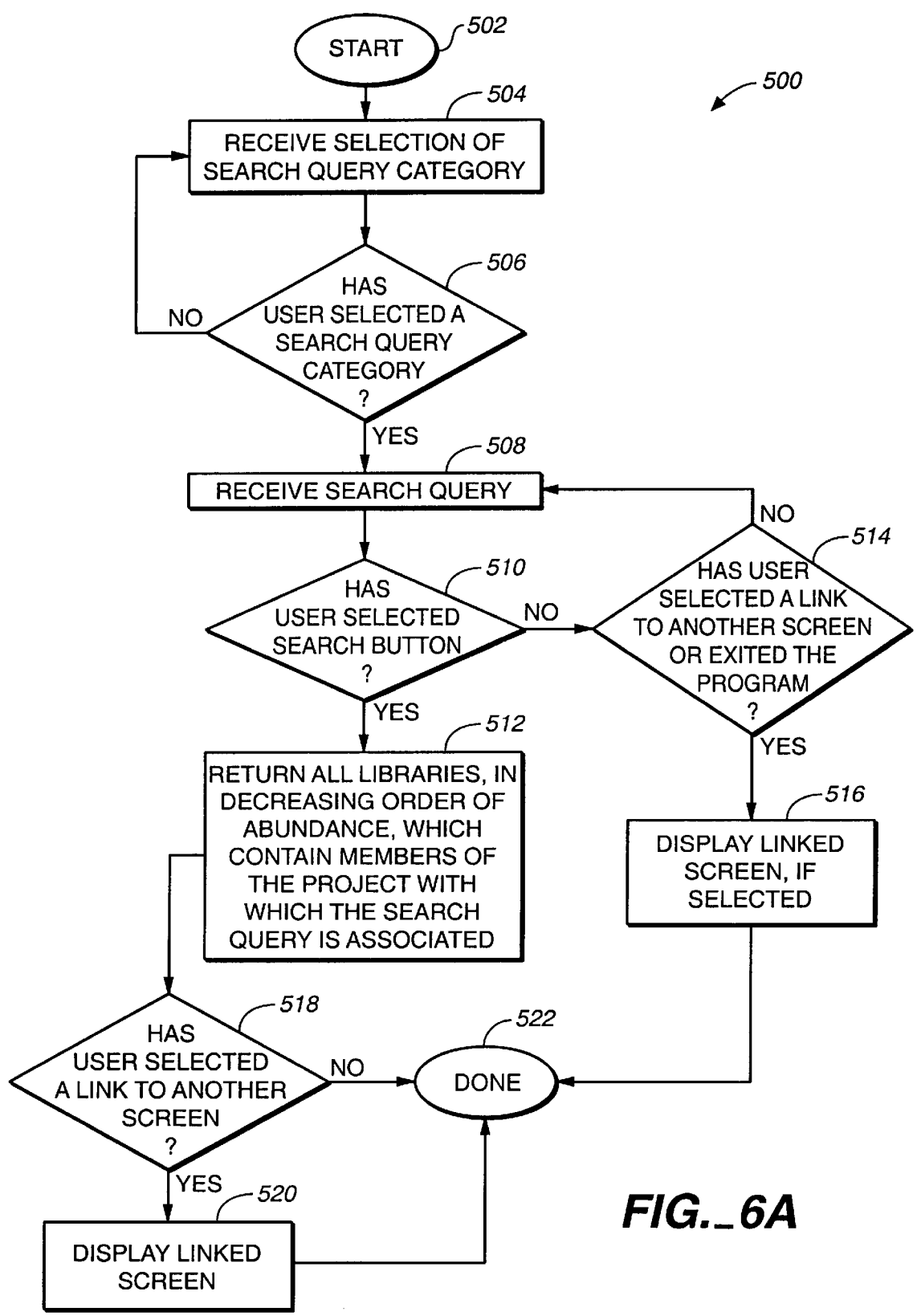
FIG._6A

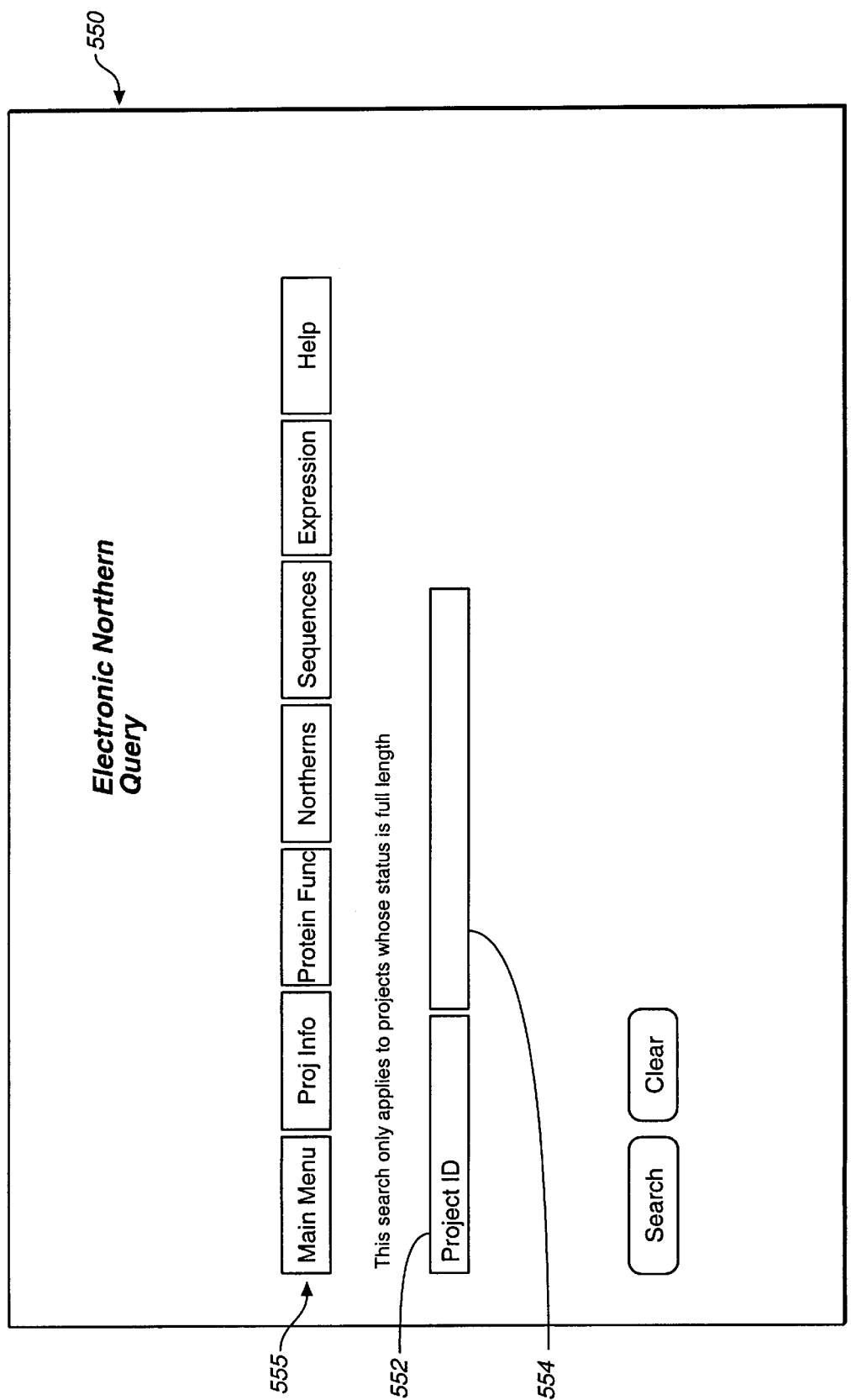

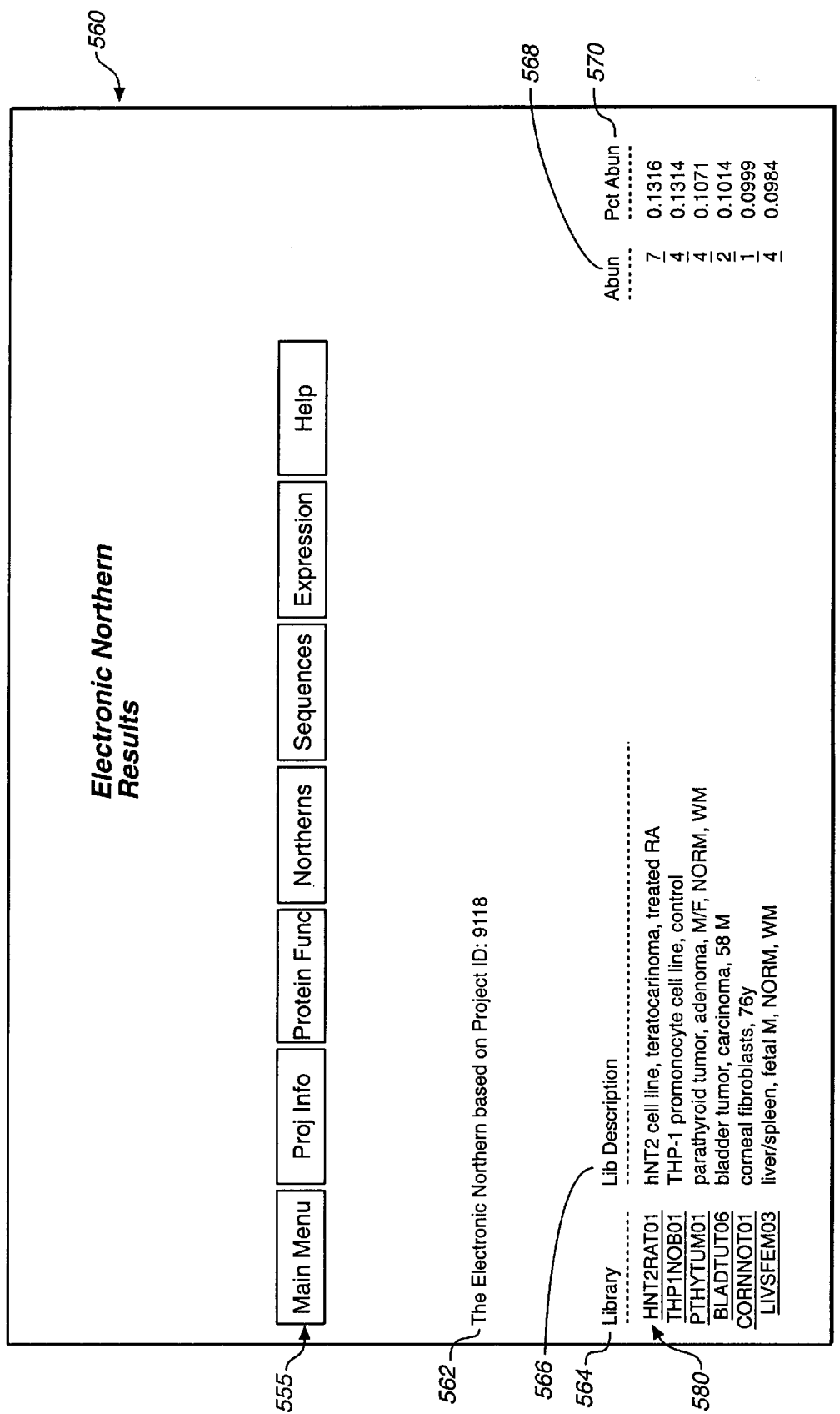
FIG._6C

Clone Information Results

| Main Menu | Proj Info | Protein Func | Northerns | Sequences | Expression | Help |

LifeSeq Clone Information based on FL Project ID: 9118
and Library: HNT2RAT01

| ClusterID | CloneID | Library | HIT ID | HIT Description | DataSource | Score | LkLbd | NumSeqs |
|-----------|---------|---------|--------|-----------------|------------|-------|-------|---------|
| 631 | 258294 | HNT2RAT01 | gI136742 | Human mRNA for protein disulfide isomera | gb96pri | 65 | -90 | 1 |
| 631 | 258295 | HNT2RAT01 | gI136742 | Human mRNA for protein disulfide isomera | gb96pri | 66 | -103 | 1 |
| 631 | 260920 | HNT2RAT01 | gI136742 | Human mRNA for protein disulfide isomera | gb96pri | 49 | -92 | 1 |
| 631 | 482163 | HNT2RAT01 | gI136742 | Human mRNA for protein disulfide isomera | gb96pri | 100 | -67 | 1 |
| 631 | 482212 | HNT2RAT01 | gI136742 | Human mRNA for protein disulfide isomera | gb96pri | 100 | -63 | 1 |
| 631 | 483418 | HNT2RAT01 | gI136742 | Human mRNA for protein disulfide isomera | gb96pri | 100 | -61 | 1 |
| 631 | 484716 | HNT2RAT01 | gI136742 | Human mRNA for protein disulfide isomera | gb96pri | 100 | -66 | 1 |

FL Clone Info returned a total of 7 row(s).

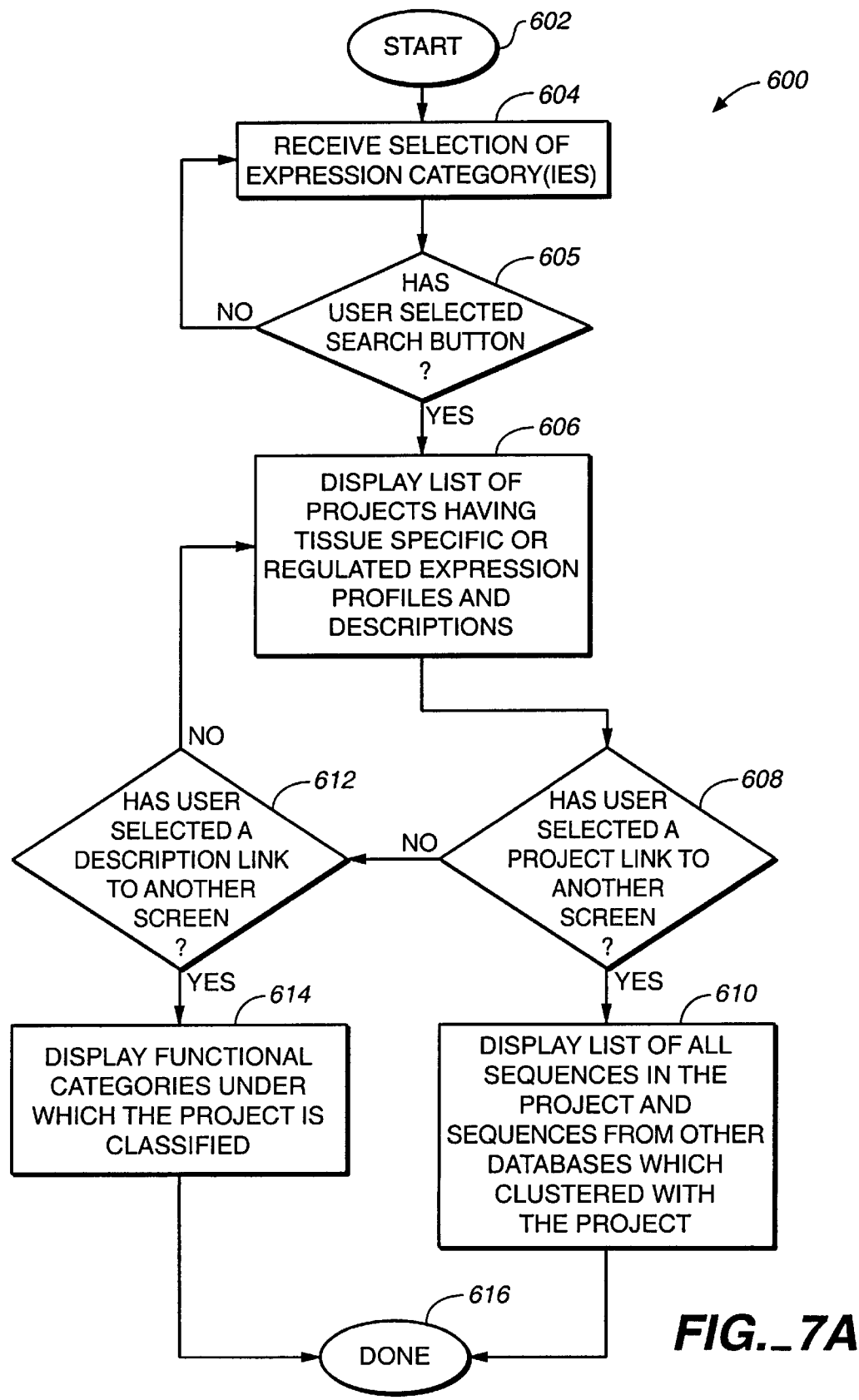
FIG._7A

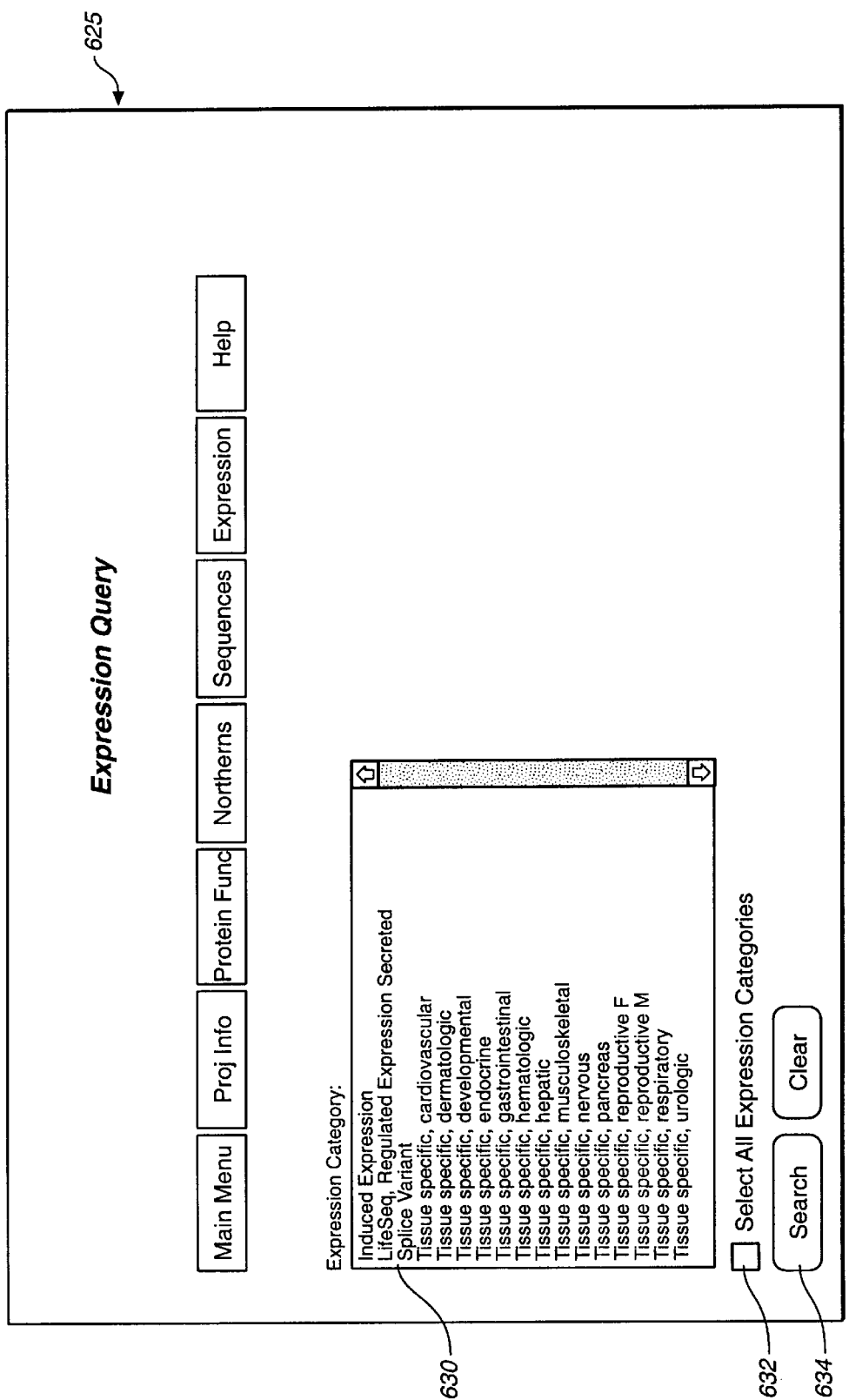

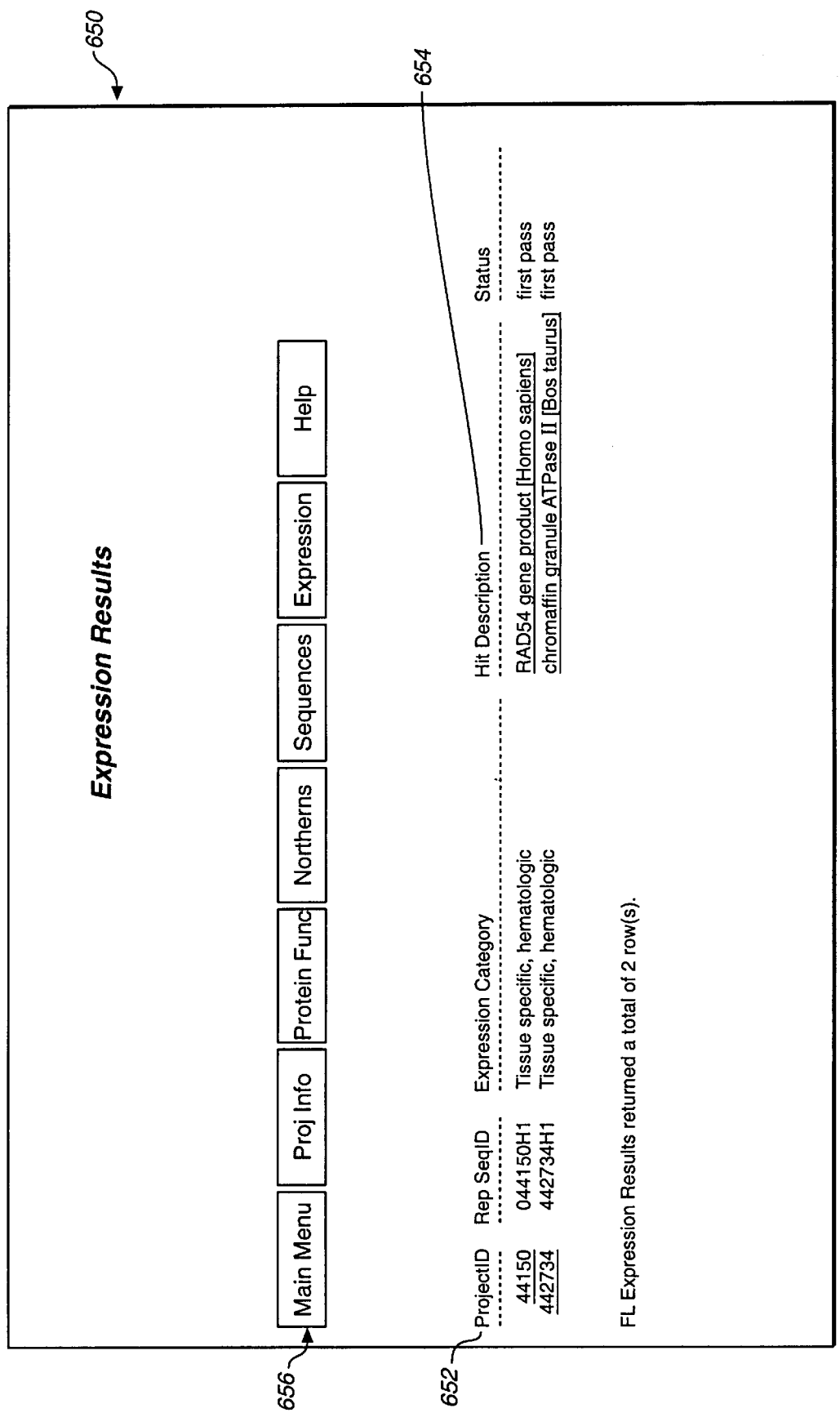
FIG._7C

5,953,727

PROJECT-BASED FULL-LENGTH BIOMOLECULAR SEQUENCE DATABASE

CROSS REFERENCE TO RELATED APPLICATIONS

This application claims priority under 35 USC § 119(e) from U.S. Provisional Patent Application Ser. No. 60/032,563 (attorney docket no. ICYTP004+), filed Dec. 12, 1996 and entitled DATA BASE CONTAINING FULL LENGTH NUCLEIC ACID SEQUENCES. This application also claims priority under 35 USC § 119(e) from U.S. Provisional Patent Application Ser. No. 60/028,284 (attorney docket no. ICYTP001+), filed Oct. 10, 1996 and entitled RELATIONAL DATABASE FOR STORING BIOMOLECULE INFORMATION. Both of these provisional applications are incorporated herein by reference in their entireties and for all purposes. In addition, this application incorporates by reference in its entirety and for all purposes application Ser. No. 08/812,290 (attorney docket no. ICYTP005) entitled DATABASE SYSTEM EMPLOYING PROTEIN FUNCTION HIERARCHIES FOR VIEWING BIOMOLECULAR SEQUENCE DATA, filed concurrently herewith.

BACKGROUND OF THE INVENTION

The present invention relates generally to relational databases for storing and retrieving biological information. More particularly the invention relates to systems and methods for providing full-length cDNA sequences in a relational format allowing retrieval in a client-server environment.

Informatics is the study and application of computer and statistical techniques to the management of information. In genome projects, bioinformatics includes the development of methods to search databases quickly, to analyze nucleic acid sequence information, and to predict protein sequence and structure from DNA or RNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers cannot and will not be able to avoid using computer resources to explore gene expression, gene sequencing, and molecular structure.

One use of bioinformatics involves studying genes differentially or commonly expressed in different tissues or cell lines (e.g. normal and cancerous tissue). Such expression information is of significant interest in pharmaceutical research. The sequence tag method involves generation of a large number (e.g., thousands) of Expressed Sequence Tags ("ESTs") from cDNA libraries (each produced from a different tissue or sample). ESTs are partial transcript sequences that may cover different parts of the cDNA(s) of a gene, depending on cloning and sequencing strategy. Each EST includes about 50 to 300 nucleotides. If it is assumed that the number of tags is proportional to the abundance of transcripts in the tissue or cell type used to make the cDNA library, then any variation in the relative frequency of those tags, stored in computer databases, can be used to detect the differential abundance and potentially the expression of the corresponding genes.

To make EST information manipulation easy to perform and understand, sophisticated computer database systems have been developed. In one database system, developed by Incyte Pharmaceuticals, Inc. of Palo Alto, Calif., abundance levels of mRNA species represented in a given sample are electronically recorded and annotated with information available from public sequence databases such as GenBank. The resulting information is stored in a relational database that may be employed to establish a cDNA profile for a given tissue and to evaluate changes in gene expression caused by disease progression, pharmacological treatment, aging, etc.

While relational database systems such as those developed by Incyte Pharmaceuticals, Inc. provide great power and flexibility in analyzing gene expression information, this area of technology is still in its infancy and further improvements in relational database systems and their content will help accelerate biological research for numerous applications.

SUMMARY OF THE INVENTION

The present invention provides relational database systems for storing biomolecular sequence information in a manner that allows sequences to be catalogued and searched according to one or more characteristics. The sequence information of the database is generated by one or more "projects" which are concerned with identifying the full-length coding sequence of a gene (i.e., mRNA). The projects involve the extension of an initial sequenced portion of a clone of a gene of interest (e.g., an EST) by a variety of methods which use conventional molecular biological techniques, recently developed adaptations of these techniques, and certain novel database applications. Data accumulated in these projects may be provided to the database of the present invention throughout the course of the projects and may be available to database users (subscribers) throughout the course of these projects for research, product (i.e., drug) development, and other purposes.

In a preferred embodiment, the database of the present invention and its associated projects may provide sequence and related data in amounts and forms not previously available. The present invention preferably makes partial and full-length sequence information for a given gene available to a user both during the course of the data acquisition and once the full-length sequence of the gene has been elucidated. The database also preferably provides a variety of tools for analysis and manipulation of the data, including Northern analysis and Expression summaries. The present invention should permit more complete and accurate annotation of sequence data, as well as the study of relationships between genes of different tissues, systems or organisms, and ultimately detailed expression studies of full-length gene sequences.

The invention provides a computer system including a database having sequence records containing information identifying one or more projects to which each of the sequence records belong. Each project groups together one or more biomolecular sequences generated during work to obtain a full-length gene sequence from a shorter sequence. The computer system also has a user interface allowing a user to selectively view information regarding one or more projects. The biomolecular sequences may include nucleic acid or amino acid sequences. The user interface may allow users to view at least three levels of project information including a project information results level listing at least some of the projects in said database, a sequence information results level listing at least some of the sequences associated with a given project, and a sequence retrieval results level sequentially listing monomers which comprise a given sequence.

A method of using a computer system and a computer program product to present information pertaining to a plurality of sequence records stored in a database are also provided by the present invention. The sequence records contain information identifying one or more projects to which each of the sequence records belong. Each of the projects groups one or more biomolecular sequences generated during work to obtain a full-length gene sequence from a shorter sequence. The method and program involve providing an interface for entering query information relating to one or more projects, locating data corresponding to the entered query information, and displaying the data corresponding to the entered query information.

Additionally, the invention provides a method of using a computer system to present information pertaining to a plurality of sequence records stored in a database. The sequence records contains information identifying one or more projects to which each of the sequence records belong. Each of the projects groups one or more biomolecular sequences generated during work to obtain a full-length gene sequence from a shorter sequence. The method involves displaying a list of one or more project identifiers, determining which project identifier or identifiers from the list is selected by a user, then displaying a second list of one or more biomolecular sequence identifiers associated with the selected project identifier or identifiers, determining which sequence identifier or identifiers from the second list has been selected by a user, and displaying a third list of one or more sequences corresponding to the selected sequence identifier or identifiers. Following the display of the third list, a determination may be made whether and which sequence from the third list has been selected by a user. If a sequence is selected, a sequence alignment search of the selected sequence against other databased sequences may be initiated, and the results of the alignment search displayed.

For Electronic Northern analysis, the invention further provides a computer system including a database having sequence records containing information identifying one or more projects to which each of the sequence records belong, each of said projects grouping one or more biomolecular sequences generated during work to obtain a full-length gene sequence from a shorter sequence. The system also has a user interface capable of allowing a user to select one or more project identifiers or project member identifiers specifying one or more sequences to be compared with one or more cDNA sequence libraries, and displaying matches resulting from that comparison.

A method of using a computer system to present comparative information pertaining to a plurality of sequence records stored in a database is also provided by the present invention. The sequence records contain information identifying one or more projects to which each of the sequence records belong, each of the projects grouping one or more biomolecular sequences generated during work to obtain a full-length gene sequence from a shorter sequence. The method involves providing an interface capable of allowing a user to select one or more project identifiers or project member identifiers specifying one or more sequences, comparing the one or more specified sequences with one or more cDNA sequence libraries, and displaying matches resulting from the comparison.

In addition, for Expression analysis, the invention provides a computer system including a database having sequence records containing information identifying one or more projects to which each of the sequence records belong, each of the projects grouping one or more biomolecular sequences generated during work to obtain a full-length gene sequence from a shorter sequence. The system also has a user interface allowing a user to view expression information pertaining to the projects by selecting one or more expression categories for a query, and displaying the result of the query.

A method of using a computer system to view expression information pertaining to one or more projects, each of the projects grouping one or more biomolecular sequences generated during work to obtain a full-length gene sequence from a shorter sequence, is also provided in accordance with the present invention. The computer system includes a database storing a plurality of sequence records, the sequence records containing information identifying one or more projects to which each of the sequence records belong. The method involves providing an interface which allows a user to select one or more expression categories as a query, locating projects belonging to the selected one or more expression categories, and displaying a list of located projects.

Finally, the present invention provides a computer system including a database having sequence records containing information identifying one or more projects to which each of the sequence records belong, each of the projects grouping one or more biomolecular sequences generated during work to obtain a full-length gene sequence from a shorter sequence. This computer system has a user interface allowing a user to selectively view information regarding said one or more projects and which displays information to a user in a format common to one or more other sequence databases.

These and other features and advantages of the invention will be described in more detail below with reference to the drawings.

BRIEF DESCRIPTION OF THE DRAWINGS

FIG. 1A is an illustration of a library having multiple clones, one of which will be selected as a "birth clone."

FIG. 1B is an illustration of various sequences relevant to a project including a gene, a first pass sequence, the birth clone, forward and reverse long read sequence, assemblages, and a full length sequence.

FIG. 1C is an illustration of how various projects are merged, if during the course of sequencing work it becomes apparent that two or more projects relate to the same gene.

FIG. 1D is an illustration of various sequence matches and associated "product scores" representing the strengths of the sequence matches.

FIG. 2A is a block diagram of a client-server Intranet for providing database services in accordance with one embodiment of the present invention.

FIG. 2B is a schematic representation of the various software documents entities employed by the FIG. 2A client-server Intranet to provide biological information in response to some user queries.

FIG. 3 is a physical data model for a gene expression relational database containing full length cDNA sequences in accordance with a preferred embodiment of the present invention.

FIG. 4 is a screen (HTML page) display presenting a Main Menu for a graphical user interface of a full length sequences database in accordance with one embodiment of the present invention.

FIG. 5A is a Project Information Query screen allowing users to enter queries about particular projects or sequences within projects.

FIG. 5B is a Project Information Results screen for displaying project information generated by the full length sequences database in response to user queries formulated on the screen of FIG. 5A.

FIG. 5C is a Sequence Information Results screen presenting sequences associated with a particular project.

FIG. 5D is a Sequence Retrieval Results screen for displaying actual amino acid or nucleotide sequences of a selected project sequence.

FIG. 5E is a process flow diagram of a user interface process by which a user can investigate sequences in a full-length project-based sequence database using a variety of search categories.

FIG. 6A is a process flow diagram of a user interface process by which a user of a full-length project-based sequence database can determine the libraries in which a given gene is expressed and its abundance.

FIG. 6B is a screen shot of a user interface HTML page provided for accepting user queries pertaining to Electronic Northerns.

FIG. 6C is a screen shot of a user interface HTML page provided to display results of a user's Electronic Northern query.

FIG. 6D is a screen shot of a user interface HTML page provided to display the results of a user's selection of a CloneID HTML link form an Electronic Northern Results screen.

FIG. 7A is a process flow diagram a user interface process by which a user of a full-length project-based sequence database can view expression information concerning the projects of the database.

FIG. 7B is a screen shot of a user interface HTML page provided for accepting user queries pertaining an Expression category.

FIG. 7C is a screen shot of a user interface HTML page provided to display results of a user's Expression query.

DETAILED DESCRIPTION OF THE PREFERRED EMBODIMENTS

1. Introduction and Relevant Terminology

Generally, the present invention provides an improved relational database for storing sequence information. The invention may be employed to investigate data from various sources. For example, it may catalogue animal sequences (e.g., human, primate, rodent, amphibian, insect, etc.), plant sequences, and microbial sequences. In the following description, numerous specific details are set forth in order to provide a thorough understanding of the present invention. It will be apparent, however, that the present invention may be practiced without limitation to some of the specific details presented herein.

The following terms are used throughout the specification. The descriptions are provided to assist in understanding the specification, but do not necessarily limit the scope of the invention.

Internal database—This is the focus database of this invention. It contains biomolecular sequences associated with a project. It may also contain information associated with sequences such as the library in which a given sequence was found, descriptive information about a likely gene associated with the sequence, etc. The database may divided into two parts: one for storing the sequences themselves and the other for storing the associated information. This database may sometimes be referred to a "local" or "enterprise" database.

The internal database may typically be maintained as a private database behind a firewall within an enterprise. However, this invention is not so limited and the internal database could actually be made available to the public. The internal database may include sequence data generated by the same enterprise that maintains the database, and may also include sequence data obtained from external sources. Examples of private internal databases include the LifeSeq™ and LifeSeq FL™ databases available from Incyte Pharmaceuticals, Inc. of Palo Alto, Calif.

Sequence database—When the internal database is designed to include separate parts, one of these may be a sequence database which contains sequences of biomolecules in the internal database.

Gene expression database—When the internal database is designed to include separate parts, one of these may be a gene expression database containing annotation information about sequences in sequence database. As noted, such information may include the library in which a given sequence was found, descriptive information about a related cDNA(s) associated with the sequence, etc.

External database—This is a database located outside the internal database. Typically, it will be maintained by an enterprise that is different from the enterprise maintaining the internal database. In the context of this invention, the external database is used primarily to obtain information about the various sequences stored in the internal database. The external database may be used, for example, to provide some descriptive information stored in the gene expression database. In a preferred embodiment, the external database is GenBank and associated databases maintained by the National Center for Biotechnology Information (NCBI), part of the National Library of Medicine. GenPept is the associated public protein-sequence database that contains all the protein databases from GenBank. Other examples of external databases include the Blocks database maintained by the Fred Hutchinson Cancer Research Center in Seattle and the Swiss-Prot site maintained by the University of Geneva.

Record—This term generally refers to a row in a database table. Each record contains one or more fields or attributes. A given record may be uniquely specified by one or a combination of fields or attributes known as the record's primary key. A "sequence record" as used herein is generally a record containing information identifying a project to the sequence record belongs, and usually also contains a plurality of attributes with information pertaining to that project.

Gene—As generally used herein, refers to a cDNA transcript of a mRNA which codes for a complete protein. The mRNA is a transcript of the coding portions of a genomic DNA gene sequence.

Library—A collection of expressed genes, with annotations, from a specific tissue or other sample.

Full-length project or just "project"—This describes one or more sequences associated with an enterprise effort to identify the entire sequence of a gene. A project is created when a clone is identified as encoding at least of a portion of a potentially interesting protein. Such a clone, referred to as the birth clone, enters a full-length sequencing program having as its goal elucidation of the full sequence of the gene containing the birth clone. As the project evolves, multiple sequences become part of the project. The birth clone becomes the first member of a project. Eventually, 5' complete sequences, assemblages of sequences, and ultimately a full-length sequence may become members of the project. Each project has a representative sequence which is generally the best consensus sequence (e.g., a full-length sequence). To simplify cataloging the projects, each project includes a unique ProjectID which is an ID number related to the project's birth clone.

First pass sequence—This is a project member having the project's initial sequence (e.g., a sequenced cDNA fragment of a gene of interest). In one embodiment it is obtained from high-throughput sequencing (HTPS). It may be an EST that has been identified as being derived from or homologous to a potentially interesting gene. It describes a partial sequence of the birth clone. In one embodiment the first pass sequence corresponds to a nucleotide alignment in GenBank but does not contain the start of a coding sequence; or has a protein alignment but does not contain the amino-terminal end of a GenPept sequence.

Assemblage—This is a project member providing a sequence (e.g., cDNA) that contains more information than the initial project sequence but is not yet full-length. The added sequence may come from assembly of overlapping clones (including the birth clone). Alternatively, additional sequences may be obtained from extension cloning or from long-read sequencing.

Long read sequence—This is a sequence of the birth clone generated from either the 3' (using e.g., M13-21 primer) or 5' (using e.g., M13 reverse primer) ends of the mRNA. If the birth clone is short enough, the forward and reverse long read sequences may overlap, thereby providing a complete sequence of the birth clone. The forward and reverse long read sequences may also be assembled with the first pass sequence to help elucidate the full birth clone sequence.

5' complete sequence—This is a project member having a sequence (e.g., cDNA) that presumptively contains the 5' terminus of the gene. In one embodiment, the 5' complete sequence is recognized as having a nucleotide alignment containing an annotated start of a coding sequence feature in GenBank or a protein alignment containing the amino-terminal end of a GenPept sequence (novel homologue or exact match).

Full-length sequence—This is a project member having an entire gene sequence coding for a polypeptide sequence. The full sequence may be recognized as one having an alignment matching the N- and C-termini of a public sequence (for example from GenPept). The match need not be exact, and may simply specify a novel homologue. The full-length sequence may be recorded as a cDNA sequence or, alternatively, as the full mRNA sequence or amino acid sequence of a polypeptide encoded by the full mRNA sequence.

Cluster—This is a group of clones related to one another by sequence homology. In one example, clusters are formed based upon a specified degree of homology and overlap (e.g., a stringency (Product Score described below) of >=50 and <=100). A project's full-length sequence may be compared against sequences from other clones (e.g., first-pass sequences in the internal database). When a sequence from the internal database overlaps part of a full-length sequence, the internal database sequence becomes part of the same project as its related full-length sequence. This allows researchers to identify clusters of related gene sequences.

Biological function—this describes the global or biological behavior and effects of a protein or peptide. Generally, a protein's biological function does not directly specify its structure or functioning at a molecular level. Rather, it specifies the protein's behavior at at least the cellular level. Examples include "cell cycle" and "DNA repair." In addition, the biological function may specify a protein's function in an even more global context such as the tissue level or the organism level. An example of a tissue level category is "apoptosis," and an example of an organism level category is "development."

Molecular function—this describes the local or chemical behavior of a protein or peptide. Generally, a protein's molecular function does not account for its functioning at biological level (e.g., a cellular, tissue, or organismal level). In fact, the molecular function may often be the same in vitro and in vivo. Examples of molecular function include "microfilaments," "chromatin" and "calcium channels."

2. Data Flow for Populating the Gene Expression Relational Database

The following description presents one preferred method for generating and collecting sequence data for a project. FIGS. 1A and 1B help illustrate the process.

Selection and processing of sequences for a database of the present invention begins by identifying a promising candidate sequence which may constitute less than a full gene sequence. Criteria for selecting such candidate sequence will be further described below. In one approach, a candidate sequence for a new project is obtained by analysis of sequence data found in an existing sequence database, for example, the LifeSeq™ database developed by Incyte Pharmaceuticals, Inc., of Palo Alto, Calif. Generally, such a source database will be populated by specifically identified and catalogued cDNA clones. An example of one process by which data for a source database may be obtained is as follows.

Messenger RNA (mRNA) is extracted from a sample under consideration (e.g., a particular tissue or cell line) and fully-complex cDNA libraries are constructed. Preferably, these libraries are generated by molecular cloning techniques well known in the art. These techniques make use of the principal flow of expressed genetic information from genomic DNA, to mRNA, to protein. That portion of a genomic DNA sequence which is ultimately expressed as protein is first converted (transcribed) to corresponding (and complementary) mRNA sequences. These mRNA sequences, representing a cell's genes, are extracted from other cellular materials by known techniques, such as affinity chromatography.

A typical cell may contain 10,000 to 30,000 unique mRNA transcripts. For complex tissues (such as brain), this number can be 100,000 or greater. Further, there are three abundance (or prevalence) classes of mRNA; (1) high (super-prevalent) species which exist at greater than 10,000 copies per cell; (2) middle (prevalent) species which exist at 100 to 400 per copies per cell; and (3) low (rare) species which are found at less than 15 unique transcripts per cell.

Clone libraries are composed of complementary DNA (cDNA). Techniques for synthesis of first-strand cDNA from mRNA are well known in the art. One suitable technique is initiated by using (1) a poly-deoxythymidine (poly-dT) primer oligonucleotide that is complementary to the characteristic poly-adenosine (poly-A) tail at the 3' end of most eukaryotic mRNA transcripts; and (2) the reverse transcriptase enzyme. Preferably, the primer used in this reaction also contains a restriction enzyme recognition cite (e.g., Not1) that permits insertion of the appropriate cloning vector. Second-strand cDNA synthesis may employ RNase to nick the mRNA/cDNA hybrid created in the reverse transcription reaction, creating priming cites for *E. coli* DNA polymerase to create second-strand cDNA. The gaps in the second strand may then be ligated together using *E. coli* DNA ligase.

After the ends of the cDNA are blunted with, for example, T4 or Pfu DNA polymerase, an adapter may be ligated into the double-stranded cDNA. This oligonucleotide, which contains a second enzyme restriction cite (usually EcoR1 or Sal1), allows for directional cloning of the cDNA once digestion is complete with the initial enzyme restriction cite (e.g., Not1) found at the 3' terminus of the cDNA. The cDNA is then size-fractionated to remove very short cDNAs which would inhibit the ability to generate highly complex libraries. Thereafter, the cDNAs, which, for the most part are complementary sequences of portions of mRNAs which code for proteins, are ligated into a plasmid vector Sequencing is an adaptation of the natural process of DNA replication. Therefore, it requires template and primer sequences. One general template preparation and sequencing protocol begins with automated picking of bacterial colonies, each of which contains a separate cDNA clone which will function as a template for the sequencing reaction. The selected colonies are placed into media, and grown overnight. The cDNA templates are then purified from the cells and suspended in water. After DNA quantification, high-throughput sequencing is performed using a sequencers, such as Applied Biosystems, Inc., Prism 377 DNA Sequencers. These "first pass," or "high-throughput" sequences are generally a partial sequence of their associated clone, starting from the 5' end of the clone. They are unique identifiers of their respective clones, and are sometimes referred to as expressed sequence tags (ESTs). As mentioned, an EST is generally about 50–300 nucleotides in length and, depending on cloning and sequencing strategy, may cover all, but more frequently a fraction, of the gene sequence. The cDNA clones from which ESTs are derived are generally part of libraries, each of which represents a collection of genomic information expressed for a given tissue or sample. Typically, libraries containing more than 1 million clones are generated. FIG. 1A is a representation of a cDNA clonal library 1, showing the cDNA clonal inserts 2 expanded from the vector portions 4 of the clones.

In order to analyze and manipulate EST information, sophisticated computer relational database systems have been developed, for example, the aforementioned LifeSeq™ database developed by Incyte Pharmaceuticals, Inc., of Palo Alto, Calif., which was described in U.S. Provisional Patent Application Ser. No. 60/028,284, filed Oct. 10, 1996, the disclosure of which was previously incorporated by reference.

The database of the present invention is concerned with fulllength gene sequences and the information generated during discovery of such full-length gene sequences. ESTs representing clones of genes of interest are selected from a source database (e.g., part of an internal database) based on several criteria. Genes of interest may include those which relate to interesting patterns of expression, such as those associated with particular biochemical functions or disease states. ESTs which demonstrate some homology to existing genes of interest, but for which no data exists in public databases are frequently selected. Moreover, genes in the rare and sometimes the prevalent abundance categories are generally selected since those genes are more likely to be tissue or system specific.

Various elements of the process for generating full-length sequences for the database of the present invention are illustrated in FIG. 1B. As noted, each full-length gene sequencing effort undertaken in conjunction with the database of the present invention is termed a "project." Each project begins with a cDNA clone 10 (represented in FIG. 1B by its sense strand) corresponding to an EST 15 selected from the source database. The EST sequence in a project may be denoted "H1" as shown in FIG. 1B. "H" stands for high throughput sequencing and "1" stands for the first such sequence in the project.

Clone 10 is generally a partial cDNA transcript of an mRNA 20 which codes for a complete protein., and may be termed a "birth clone." For convenience, this birth clone 10 may retain the sequence ID number assigned to it in the source database or library from which it is taken. Each project may be initially identified by its birth clone ID.

A full-length sequencing project begins with a determination of whether or not the 5' end of the EST 15 incorporates or is close to the 5' end of the mRNA 20. If this is the case, it indicates that the birth clone likely contains the entire coding region of the gene of interest, and it is a simple matter to sequence the entire length of the clone by the long-read, and possibly the sub-cloning methods described below. More frequently, however, the 5' end of the EST will not correspond to the 5'end of the mRNA, and further steps will be required to determine the complete sequence of the gene.

In either event, the first step in the full-length sequencing process is long-read sequencing from both the 5' and 3' ends of the birth clone. Long-read sequencing uses primers (e.g., M13-21 primer gives 3'("reverse") sequence and M13 reverse primer gives 5' ("forward") sequence) complementary to the known vector sequences adjacent to the cDNA clonal insert, and generally has an approximately 600 base read length due to sequence reaction conditions and electrophoretic gel resolution limitations. When a birth clone is approximately one kilobase (kb; 1000 bases) in length, long-read sequencing from both ends of the clone will generally be sufficient to determine the entire sequence for the clone, since the ends of a 5' long-read sequence 30 and a 3' long-read sequence 35 obtained will overlap in the middle of the birth clone sequence. The project's first forward long read sequence in a project is denoted "F1" and its first reverse long read sequence is denoted "R1."

When the 5' long-read sequence 30 and the 3' long-read sequence 35 do not overlap, it is an indication that the birth clone may be more than approximately 1 kb in length. In this case, the sequence of the birth clone may be determined by well known molecular biological techniques such as sub-cloning, which breaks the birth clone into smaller pieces, followed by long-read sequencing to determine the complete sequence of each sub-clone (not shown). The sequences of these sub-clones may then be combined to obtain a complete consensus sequence of the original birth clone. Alternatively, full length sequence coverage may be obtained from other cDNA library sequences, such as those found in the previously noted LifeSeq™ database developed by Incyte Pharmaceuticals, Inc., of Palo Alto, Calif. The consensus sequence of the birth clone obtained by subcloning and/or forward and reverse long reads may be denoted "C."

Generally, the birth clone will include coverage of the 3' end of the cDNA. This may be confirmed by the presence of several consecutive thymidine nucleotides 12 at the 3' end of the antisense strand of the clone (not shown). These nucleotides are complementary to the characteristic poly-A nucleotide tail 22 present on the 3' end of mRNA transcripts. The 3' end of the clone is present in virtually all birth clones since the presence of the distinctive poly-A tail 22 in mRNA is used to design a complementary poly-T oligonucleotide primer as an initiation point for cDNA synthesis. However, some cDNAs will generally be generated using a random primer, and will therefore not have a poly-A tail.

Once the presence of the birth clone's 3' end is confirmed, the sequencing project continues towards the 5' end of the cDNA clone. "Extension" of the birth clone 10 into the full expression sequence of the gene may be conducted in a number of ways. In one method, two primers 40 are designed to correspond to the ends of the of the known birth clone sequence and to anneal to DNA in a cDNA library so as to initiate extension away from the known cDNA sequence. The primers are added to a cDNA library with appropriate enzymes and extend through additional DNA sequence to produce PCR products 42, 44, 46. These PCR products are subsequently purified and sequenced to provide new sequences 50, 52, 54. The new sequences are then compared with the known partial cDNA sequence for areas of overlap, and the sequence is extended beyond the overlapping areas to provide longer DNA sequence. This technique is described more fully in U.S. patent application Ser. No. 08/487,112, filed Jun. 7, 1995, entitled "Method for Obtaining Full-Length cDNA Sequences," which is incorporated by reference herein in its entirety.

In addition, it may be possible to extend the birth clone 10 by comparing its now known sequence against internal or external sequence databases (for instance, using a BLAST searching algorithm) in order to locate homologous sequences (e.g., sequences 60 and 62 in FIG. 1B) which cluster with or overlap with the known birth clone sequence.

The extension sequences may be identified as containing the 5'terminus of the full mRNA sequence by comparing extension sequences' 5' ends with those of the known gene associated with the project. For example, if the first pass EST was selected for the project based upon its match to a GenBank gene, then the 5' ends of the extension sequences are compared against the corresponding end of the most closely related GenBank gene (or an amino terminus of a corresponding protein). If there is a strong homology, then it is assumed that the 5' end of the project's gene has been located.

Sequences in addition to the birth clone determined either by molecular cloning and sequencing methods or by additional database searching are assembled with the original birth clone to construct a consensus sequence 70 that is the full sequence of the gene. Except where the birth clone contains the entire sequence of a cDNA, the consensus sequence 70 will be an electronic sequence, existing as a composite sequence of discrete cDNA fragments generated from more than one template. Based on this sequence, however, an actual clone of the gene sequence may be synthesized by known methods. This physical gene clone may then be used in the laboratory for expression of the protein and functional assays for product (i.e., drug) development.

In a particular embodiment of the present invention, cDNA sequences which contain more information than the birth clone, but which are not yet full-length may be specifically identified. These sequences may be assemblages of clustering or overlapping of additional clones from internal or external databases or from extension cloning and further long-read sequencing. As noted above, in this particular embodiment, a cDNA sequence which is less then a full-length sequence, but which contains a nucleotide alignment corresponding to an annotated start of a coding sequence having a protein alignment containing the amino-terminal end of a GenPept sequence, is referred to as 5' complete. A sequence is considered full-length once it has been assembled and edited and it has been confirmed that the sequence codes for a polypeptide sequence with an alignment matching the N-terminus and C-terminus of a GenPept sequence (novel homologue or exact match).

There are generally several separate concurrent projects proceeding in conjunction with the database of the present invention attempting to sequence genes from birth clones. Sometimes, as these projects progress, it becomes clear that two birth clones are in fact part of the same gene. In this event, the two projects will be merged and will continue under the ID of the project that has been most active, for example. This process is illustrated in FIG. 1C where ProjectIDs 37521 and 57280 are merged into ProjectID 8118 as time proceeds from the bottom to the top of the figure.

Throughout these projects, sequence data may be continuously provided to the database of the present invention where a user of the database may retrieve, analyze and manipulate information about a particular birth clone, extension or project even before the full-length sequence of the gene has been determined. The new sequences may be continuously compared (e.g., using a BLAST algorithm) against external (e.g., public, such as GenBank) databases and annotated based on located matches ("hits"). Sequences for which no matches are located may be identified, usually as a unique sequence, with a proprietary designation.

"Clustering" may be performed with the sequence data after or prior to the determination of the full-length sequence of the gene. For instance, a sequence thought to be associated with a particular molecular or biological function in one tissue might be compared (e.g., using a BLAST algorithm) against another library or database of sequences. This type of search, an electronic version of the analogous molecular biological technique known as Northern blotting, is useful to look for homologous, and presumably functionally related, sequences in other tissues or samples. The sequences showing sufficient homology with the representative project sequence are considered part of a "cluster" and become associated with the project.

A number of computer platforms can be used to perform the necessary calculations for various algorithmic processes employed in the project (e.g., assembling and clustering the sequences). For example, a number of computer workstations from a variety of manufacturers can be used. In particular, workstations produced by Silicon Graphics, Inc. (SGI) of Mountain View, Calif. and multiprocessor (e.g. 12 processor) Alpha™ systems manufactured by Digital Electronics Corporation (DEC) of Maynard, Mass. have been found to be suitable for performing such calculations.

3. Matching Techniques

As noted above, the assembling and clustering (whether or not used for assembling) techniques employed in a project require some mechanism for assessing the homology and overlap of two sequences. Various techniques may be employed for this purpose and some will now be described. These techniques may also be employed to assess the strength of a match or "hit" of an internal database sequence in an external database.

Generally, for clustering/matching to be valid, two sequences should possess overlap regions of identical base pairs or at least close homology. To discover such overlap, the clustering/matching procedure may employ a sequence alignment algorithm such as BLAST (Basic Local Alignment Search Tool) or the Smith-Waterman algorithm. Both of these algorithms look for regions of ungapped similarity between two sequences (although Smith-Waterman handles gaps rather well). To do this, they determine (1) alignment between similar regions of the two sequences, and (2) a percent identity between sequences. The alignment is calculated by matching, base-by-base, the regions of substantial similarity. In these regions, identical bases are scored with a value of +5 and mismatched bases are scored with a value of −4 (for nucleic acids). Regions of contiguous bases having sufficiently high score are deemed High Scoring Pairs ("HSPs"). In BLAST, the score of the best HSP (referred to as the BLAST Score) is presented as an output. In addition, for each HSP, the percent identity is calculated and presented as a BLAST output, as is the alignment. Finally, a P-Value for each HSP is calculated. As is known to those of skill in the art, the P-Value represents the probability that the observed similarity resulted from a random occurrence. Lower P-Values indicate a greater confidence that the observed similarity is not due to a random event.

In a preferred embodiment, each new sequence is compared to every usable sequence already in the internal database using BLAST. An ad hoc score, called the "Product Score," is calculated for every matched pair of sequences. The Product Score represents a normalized summary of the BLAST output parameters and is used to represent the quality of an alignment between a query and matched sequence.

Specifically, the Product Score is a normalized value between 0 and 100 indicating the strength of a BLAST match; it represents a balance between fractional overlap and quality in a BLAST alignment. For nucleic acids, the Product Score is calculated by dividing the BLAST score by 5 times the length of the shorter of the two sequences being compared, then multiplying this result by the Percent Identify over the BLAST alignment. The expression for product score is PS=(BLAST Score·Percent Identity)/(5·minimum(length(Seq1),length(Seq2)))

As shown, the BLAST score is divided by 5 and then multiplied by the Percent Identity over the BLAST alignment. Dividing this number by the length of the shorter sequence (including all HSPs) normalizes the score such that a perfect alignment (over the entire length of the shorter sequence) gives a Product Score of 100.

For a protein match, the Product Score is adjusted by multiplying the minimum length value by 3 (the equivalent of the corresponding codon triplet) and using the typical BLAST match score for proteins (approximately 5.3).

Because the Product Score is derived from BLAST alignments, it is sensitive to (1) fraction overlap, (2) percent identity, and (3) insertions and deletions. It attempts to balance fraction overlap with the Percent Identity in an alignment. The greater the overlap in the alignment, the lower the Percent Identity needed to reach a given Product Score. Referring to FIG. 1D, a Product Score of 100 is produced only for 100% identity over the entire length of the shorter of the two sequences being compared. A Product Score of 70 can be produced either by 100% identity and 70% overlap at one end, or by 88% identity and 100% overlap at the other. Similarly, a Product Score of 50 is produced by the range of alignments between 100% identity and 50% overlap, and 79% identity and 100% overlap. A Product Score of 30 would be produced by alignments between 100% identity and 30% overlap, and 69% identity and 100% overlap.

In a preferred embodiment, the Product Score serves two purposes. First, it is used in the clustering process to measure the quality of a match between all possible pairs of sequences. Sequences that overlap with a Product Score greater than a particular "stringency threshold" (50 or 70 in a specific embodiment) are grouped as members of the same cluster. Second, it represents the quality of the match between a sequence and its naming GI (i.e., GenBank sequence identifier). Preferably, the Product Scores associated with this second calculation are stored in the gene expression database.

In sequence clustering, if a BLAST match has a Product Score above the given specified stringency, then the two matched sequences will be in the same cluster. If two sequences are not in the same cluster, then they do not match with a Product Score above the stringency threshold. The higher the Product Score threshold, the more stringent the criteria for clustering. Thus, at stringency 70, fewer sequences will cluster (and the total number of clusters will be greater) than at stringency 50.

Other clustering measures besides product score may be employed. Examples of such techniques are described in U.S. Provisional Patent Application Ser. No. 60/028,284, previously incorporated by reference.

4. The Database Environment

FIG. 2A depicts a network system 130 suitable for storing and retrieving information in relational databases of the present invention. Network 130 includes a network cable 134 to which a network server 136 and clients 138a and 138b (representative of possibly many more clients) are connected. Cable 134 is also connected to a firewall/gateway 140 which is in turn connected to the Internet 142.

Network 130 may be any one of a number of conventional network systems, including a local area network (LAN) or a wide area network (WAN), as is known in the art (e.g., using Ethernet, IBM Token Ring, or the like). The network includes functionality for packaging client calls in a well-known format (e.g., URL) together with any parameter information into a format (of one or more packets) suitable for transmission across a cable or wire 134, for delivery to database server 136.

Server 136 includes the hardware necessary for running software to (1) access database data for processing user requests, and (2) provide an interface for serving information to client machines 138a and 138b. In a preferred embodiment, depicted in FIG. 2A, the software running on the server machine supports the World Wide Web protocol for providing page data between a server and client.

Client/server environments, database servers, and networks are well documented in the technical, trade, and patent literature. For a discussion of database servers and client/server environments generally, and SQL servers particularly, see, e.g., Nath, a., *The Guide To SQL Server*, 2nd ed., Addison-Wesley Publishing Co., 1995 (which is incorporated herein by reference for all purposes).

As shown, server 136 includes an operating system 150 (e.g., UNIX) on which runs a relational database management system 152, a World Wide Web application 154, and a World Wide Web server 156. The software on server 136 may assume numerous configurations. For example, it may be provided on a single machine or distributed over multiple machines.

World Wide Web application 154 includes the executable code necessary for generation of database language statements (e.g., SQL statements). Generally, the executables will include embedded SQL statements. In addition, application 154 includes a configuration file 160 which contains pointers and addresses to the various software entities that comprise the server as well as the various external and internal databases which must be accessed to service user requests. Configuration file 160 also directs requests for server resources to the appropriate hardware—as may be necessary should the server be distributed over two or more separate computers.

Each of clients 138a and 138b includes a World Wide Web browser for providing a user interface to server 136. Through the Web browser, clients 138a and 138b construct search requests for retrieving data from a sequence database 144 and/or a gene expression database 146. Thus, the user will typically point and click to user interface elements such as buttons, pull down menus, scroll bars, etc. conventionally employed in graphical user interfaces. The requests so formulated with the client's Web browser are transmitted to Web application 154 which formats them to produce a query that can be employed to extract the pertinent information from sequence database 144 or gene expression database 146.

In the embodiment shown, the Web application accesses data in gene expression database 146 by first constructing a query in a database language (e.g., Sybase or Oracle SQL). The database language query is then handed to relational database management system 152 which processes the query to extract the relevant information from database 146. In the case of a request to access sequence database 144, Web application 154 directly communicates the request to that database without employing the services of database management system 152.

The procedure by which user requests are serviced is further illustrated with reference to FIG. 2B. In this embodiment, the World Wide Web server component of server 136 provides Hypertext Mark-up Language documents ("HTML pages") 164 to a client machine. At the client machine, the HTML document provides a user interface 166 which is employed by a user to formulate his or her requests for access to database 146. That request is converted by the Web application component of server 136 to a SQL query 168. That query is used by the database management system component of server 136 to access the relevant data in database 146 and provide that data to server 136 in an appropriate format. Server 136 then generates a new HTML document relaying the database information to the client as a view in user interface 166.

While the embodiment shown in FIG. 2A employs a World Wide Web server and World Wide Web browser for a communication between server 136 and clients 138a and 138b, other communications protocols will also be suitable. For example, client calls may be packaged directly as SQL statements, without reliance on Web application 154 for a conversion to SQL.

When network 130 employs a World Wide Web server and clients, it must support a TCP/IP protocol. Local networks such as this are sometimes referred to as "Intranets." An advantage of such Intranets is that they allows easy communication with public domain databases residing on the World Wide Web (e.g., the GenBank World Wide Web site). Thus, in a particular preferred embodiment of the present invention, clients 138a and 138b can directly access data (via Hypertext links for example) residing on Internet databases using a HTML interface provided by Web browsers and Web server 156.

Bare in mind that if the contents of the local databases are to remain private, a firewall 140 must preserve in confidence the contents of a sequence database 144 and a gene expression database 146.

In a preferred embodiment, the gene expression and sequence databases include a plurality of tables not directly associated with the full-length project information described above. In one specific embodiment, these tables provide information about ESTs which as noted above are short sequences (about 50–300 base pairs) of cDNA transcribed from mRNA. As noted, these EST sequences may be used to assemble or cluster with full-length sequences. An example of an EST database is the LifeSeq™ database available from Incyte Pharmaceuticals, Inc. and described in U.S. Provisional Patent Application Ser. No. 60/028,284, previously incorporated by reference.

In a preferred embodiment, sequence database 144 is a flat file database including separate partitions for full-length nucleotide sequences and full-length peptide (amino acid) sequences. If it contains other information such EST sequences, these may provided in a separate partition. Other approaches include partitioning the sequence data according to species such as human, primate, rodent, etc. Still further, separate partitions may be provided for sequences that have been found to be unique to the local database (i.e., sequences that did not have any hits in an external database such as GenBank).

Preferably, the information in gene expression database 146 is stored in a relational format. As mentioned, it may include tables for both full-length projects and ESTs. In Oracle™ databases, for example, the various tables are not physically separated, as there is one instance of work space with different ownership specified for different tables. In Sybase™ databases, in contrast, the tables for the full-length projects and the table for ESTs may be physically segregated into different "databases."

One specific configuration for network 130 for multiple users provides both the Gene Expression and Sequence databases on the same machine. If there is a high volume of sequence searching, it may be desirable to have a second processor of similar size and split the application across the two machines to improve response time.

A suitable dual processor server machine may be any of the following workstations: Sun—Ultra-Sparc 2™ (Sun Microsystems, Inc. of Mountain View, Calif.), SGI—Challenge L™ (Silicon Graphics, Inc. of Mountain View, Calif.), and DEC—2100A™ (Digitial Electronics Corporation of Maynard, Mass.). Multiprocessor systems (minimum of 4 processors to start) may include the following: Sun—Ultra Sparc Enterprise 4000™, SGI—Challenge XL™, and DEC—8400™. Preferably, the server machine is configured for network 130 and supports TCP/IP protocol.

Depending upon the workstation employed, the operating system may be, for example, one of the following: Sun—Sun OS 5.5 (Solaris 2 5), SGI—IRIX 5 3 (or later), or DEC—Digital UNIX 3 2D (or later).

The databases of this invention may be downloaded via a 4×4 Gb+FWSCSI−2, Fiber Link Raid Units 2O Gb+, or 4 DAT Tape Drive. A CD ROM drive may also be acceptable.

The client machine may be, for example, a Macintosh™ (Apple Computer Inc. of Cupertino, Calif.), a PC, or a Unix workstation. It should also be TCP/IP capable with a Netscape Web Browser.

The network may include a 10-base-T connection, be TCP/IP capable, and provide access to Internet for HTML hyperlinks to NCBI.

5. Model of the Gene Expression Relational Database

Turning now to FIG. 3, a block diagram is shown of a physical data model 200 for a gene expression relational database 146 in accordance with one embodiment of the present invention. Each block represents a separate relational table provided in database 146. Relationships between records in the various tables are indicated by lines between related tables, with one-to-many relationships indicated by branches. For example, each record in a table FL_Sequences 204 has a one to many relationship with the records in a table 206 labeled "FL_ProjAllSeq". In contrast, each record in the FL_Sequences table 204 has a one to one relationship with the records in a table 208 denoted "FL_ProjectSequences." Optional relationships are indicated by circles in the connecting lines.

The sequences found in the FL_Sequences table 204 represent all sequences associated in any way with a given full-length project. This includes sequences that are generated to form the project itself (i.e., those sequences used to assembly the full-length sequence) as well as sequences clustered with the representative sequence from the full-length project. The primary key of table 204 is the SequenceID for each sequence.

A table 210 named "FL_Project," in contrast, has a unique ProjectID (FL_ProjectID) as its primary key. Thus, it includes a single record for each full-length project. The attributes of records in table 210 include a representative sequence ID for the project, and a hit ID and hit type for the representative sequence. The hit ID refers to an identifier for a hit against an external database (e.g., GenBank). In a preferred embodiment, the hit ID is simply the ID used by GenBank (or other external database) to identify the sequence that has been hit. The hit type is "g" for a GenBank ID. Together the hit type and hit ID uniquely specify the external database "hit" sequence. The FL_Project table 410 also includes project Status field which may have the values "first pass", "assemblage", "5' complete", or "full-length" as described above. Finally, the FL_Project table 410 includes "Expression" and "ExpressionID" fields. These represent the expression categories in which a project might fall, for example, "Induced Expression" or "Tissue specific, cardiovascular."

In the FL_Sequences table, attributes other than the SequenceID (primary key) include a CloneID, various sequence related attributes, various BLAST related attributes (for sequences having a hit against an external database), various external hit attributes, a sort order, an amino acid flag, and a protein function hit flag. As for the CloneID, note that multiple sequences can be provided for a given clone. The SeqType field specifies whether the project sequence is full-length, expression, etc. The SeqCoverage field specifies whether the 5' coverage is complete or not. The SeqLength field specifies the sequence length in number of base pairs. The Hit_Description_Short field contains an abbreviated version of the description from the external database. The Hit_DataSource field references a specific database within GenBank, for example. Examples include GenBank rodent database (gbrod) and GenBank primate database (gbpri). The hit description field is preferably an annotated description of each hit taken from the public database. The hit description may be generated in house or simply taken from the description provided in the public database.

The Sort_Order field has a different value for each sequence type and is used by the system to determine the sort order when sequences are displayed. The AminoAcid_YN field is a flag for amino acids. When the sequence at issue is an amino acid, this field is set to "Y". Finally, the PFHit_YN field is a flag for protein function hierarchies. If a sequence has an associated protein function category, the flag is set to "Y".

A table 212 denoted "FL_NorthernAbun" and a table 214 denoted "FL_NorthernClone" include the necessary information to display the results of an electronic northern query. The fields contained in the FL_NorthernAbun table 212 include the FL_ProjectID and a LibraryID which together form the primary key for this table. In a preferred embodiment, the LibraryID specifies the library in which a full-length sequence of a project was found. Other attributes in table 212 include an abundance field specifying how many clones in the specified project occur in the specified library and the percent abundance specifies the abundance attribute divided by the total number of clones in the library.

The fields contained in the FL_NorthernClone table 214 include the project and library IDs as the primary key and a CloneID. In a preferred embodiment, an electronic Northern query is handled as follows. The user enters a ProjectID or a CloneID, and the system returns an electronic Northern results screen listing the ProjectID number or CloneID number in the header. The Northern results page also includes a listing of all libraries in which the full-length sequence associated with the selected project or clone appeared. Each entry in this list specifies the library ID, a library description, and abundance of the selected sequence within the library and a percentage abundance of that sequence within the library. Some or all of the information returned in the Northern results screen may be from outside of the project database, for instance, Incyte Pharmaceutical's LifeSeq™database.

Tables 206 and 208 (FL_ProjAllSeq and FL_ProjectSequences, respectively) are employed to facilitate the join operations required to handle sequence information queries in which a user wishes to view those sequences associated with a particular project. Both tables 206 and 208 include only ProjectID and sequence ID fields. As explained below, a user may specify that a selected project be displayed with only those sequences required to assemble a project representative sequence or, alternatively, include the sequences employed in both the assembly procedure and the clustering procedure. If the user requests both the clustering and assembly sequences, then table 206 is employed in the join operation. In contrast, if the user requests only those sequences used to assembly the representative sequence within the project, then table 208 is employed. This is because table 208 is populated with only the representative sequence and associated sequences used to construct the representative sequence associated with the given project. In contrast, table 206 includes all sequences, employed during assembly and clustering, associated with a given project.

A table 216 denoted "FL_Project AKA" includes a "merged ProjectID" field and a ProjectID field. This table is provided to allow continuity between sequential data releases in which two projects are merged into a single project. Plus, if a user enters a ProjectID associated with a project that has been merged with another project, the system will still recognize the old ProjectID and return information associated with the merged project. Further, the user will automatically receive his or her desired information without knowing ahead of time that the desired project had merged.

A table 218 denoted "FL_ExternalHit" includes information pertaining to the "hits" against public databases. Specifically, if a sequence within the FL_Sequences table 204 matches with sufficient specificity a record in a public database such as the GenBank or Blocks databases, then the match from that public database is provided as a record in table 218. Each record in table 218 includes a hit ID, a hit type, and a hit description. The hit ID and hit type attributes together specify the primary key of this table.

A table 220 denoted "FL_PFExternalHit" includes records which tie external hits to specific protein function hierarchies. These hierarchies and their applications will be described in more detail below. The records in table 220 include the hit ID and hit type as described above, and in addition a PF_ID (protein function identifier) which uniquely specifies each category in the protein function hierarchies. Note that the relation between table 218 and 220 is a one to many relationship. This is because each unique hit from a public database (presented in table 218) may fall under multiple categories within the protein function hierarchies allowed in table 220. The primary key of table 220 includes a combination of PF_ID, hit ID, and hit type.

A table 222 denoted "FL_ProteinFunction" uniquely specifies each protein function category within the one or more hierarchies supported in this invention. The records of table 222 include a protein function identifier (PF_ID) which uniquely identifies the categories of the protein function hierarchies. This value may be displayed to users viewing protein hierarchy information. In addition, the records of table 222 include a protein function type (PF_Type) which uniquely specifies which of the various hierarchies the particular category falls under; an enzyme hierarchy, a molecular function hierarchy or a biological function hierarchy, for example. The combination of PF_ID and PF_Type form the primary key. Still further, the records of table 222 include a protein function description attribute (PF_Description) and a protein function full identifier (PF_Full_ID). The protein function description attribute includes a short textual description of the associated category. For example, non-histone chromatin proteins may be specified in the description field. The full ID may be used to internally identify the categories. Note that the relationship between the records in table 222 and those in table 220 is a one to many relationship. This is because each category within the protein function hierarchies may be represented by multiple hits from a public database.

Finally, a table 224 denoted "FL_version" includes various pieces of information regarding the software release. As shown, the record in this table includes the attributes software product (e.g., a full-length product), a software version number, and a data release month and year. This last field is necessary because a given version of a software product may have multiple data releases. In other words, the entity releasing the software (or another entity) may periodically update the data sequences and other data included in the relational database. When such updates occur, the data release month and year field of table 224 must be updated.

6. Graphical User Interface for Full-Length Sequences Database

In a preferred embodiment, the invention is provided together with a suite of functions made available to users through a collection of user interface screens (e.g., HTML pages). Typically, the interface will have a main menu page from which various lines of query can be followed. Of particular relevance to the present invention is a main menu page which allows users to travel toward information regarding protein functions.

FIG. 4 presents one such main menu page 302 which may be employed in a database having a full-length sequences contained therein. As shown menu page 302 includes buttons for accessing the following lines of query: protein function (button 304), project information (button 306), Northern (button 308), expression (button 310), and sequence database (button 312).

If a user selects button 304, he or she will be presented with a list of categories from one or more protein function hierarchies. One suitable format for this information is a Protein Function Query page which allows a user to select one or more categories from the hierarchy(ies) to bring up those sequences in the database that meet criteria for grouping the selected categories. This line of query is described in more detail in a companion patent application Ser. No. 08/812,290 (attorney docket no. ICYTP005), filed concurrently herewith and previously incorporated by reference.

Should the user select button 306 (project information), he or she will receive a Project Information Query screen (such as shown in FIG. 5A). In a preferred embodiment, the user can enter a full-length Project identifier in this query screen and the system will return a list of information about the selected project (e.g., the sequence members of the project, the project status, etc.). Alternatively, the user may enter a particular clone identifier, hit description, etc., and in turn receive a listing of all projects containing members meeting the entered criteria.

When the system determines that button 308 (an Electronic Northern analogous to a Northern Blot) has been selected, it will allow the user to investigate expression occurrence and abundance levels for a particular sequence. For example, a user may enter a Project identifier in a Northern query screen (such as shown in FIG. 6B. The system may then return all libraries, in decreasing percent abundance (percentage of total sequences from library that correspond to members of the identified project) that contain members of the project.

If the user should select the button 310 (Expression), the database system will allow the user to query projects by expression category. For example, expression profiles pre-designated as being of special interest may include: Induced expression, regulated expression, secreted, splice variant, and the following tissue specific categories: cardiovascular, dermatologic, developmental, endocrine, gastrointestinal, hematologic, hepatic, musculoskeletal, nervous, pancreas, reproductive—female, reproductive—male, respiratory and urologic. A user may select from one to all categories in order to return information about the projects in each selected category. Other expression categories may also be designated.

The project information, Northern and expression lines of query are described in more detail below.

Finally, when the system determines that the user has selected button 312 (Sequence Database), it allows the user to retrieve actual amino acid hand nucleotide sequences for given Sequence IDs. It also allows the user to perform sequence alignment searches (e.g., BLAST, FASTA) against various sequence databases (typically external databases), and to assemble nucleotide sequence fragments from a cluster and view how they overlap with each other.

Preferably, the user interface employed with this invention possesses similar attributes to interfaces for other sequence databases (besides a full-length projects database). Examples of other databases including similar interfaces might include (1) a general purpose short sequence database (containing for example ESTs as in the case of Incyte Pharmaceutical's LifeSeq™ database and interface), (2) a microbial genomic sequences database (such as Incyte Pharmaceutical's PathoSeq™ database and interface), and a plant genomic sequences database (such as Incyte Pharmaceutical's PhytoSeq™ database and interface). The "look and feel" of each of these databases preferably will resemble one another. For example, each might contain a commonly formatted collection of query buttons as shown as buttons 304, 306, 308, 310, and 312 in the main menu page of FIG. 4. As a result the system may bring one of multiple available "query" screens, each commonly formatted to allow the user to formulate his or her query. Upon execution of this query, the system may present an appropriate results screen (again of common format) presenting the results of the executed query.

By providing these features as a common interface spanning multiple sequence databases, users familiar with one database interface can quickly learn to navigate through related databases. Thus, they will be able to leverage their knowledge of formulating appropriate queries and locating desired sequence information obtained from working with an initial database (e.g., the LifeSeq™ database). This is the motivation behind providing any standard. In this case, the inventors have recognized that sequence database interfaces currently available have disparate looks and feels. By standardizing the look and feel of multiple sequence databases, the inventors have brought a needed consistency to the sequence database industry.

7. The Project Information User Interface

In a preferred embodiment, the database of the present invention is preferably project-orientated. That is, the sequence data populating the database is obtained through one or more biomolecular sequencing projects, such as those described above in Section 2, and the data may be catalogued in the database according to one or more project affiliations. In this way, a user may retrieve and use information from the database by referencing a particular project or group of projects, or may obtain information relating to a particular project or projects in the database by referencing particular information which belong to the project or projects.

The data flow and population of the gene expression relational database of a preferred embodiment of the present invention have been described above. From this description, one of ordinary skill in the art will understand that the database contains records relating to sequence data for one or more genes whose full-length sequence has been (or is being) determined from a shorter sequence, including nucleic acid sequences for genes of interest in various stages of completion. Each of these sequence records will contain information identifying a project to which the sequence record belongs, and usually also contains a plurality of attributes with information pertaining to that project, such as matches to external database sequences, and annotations indicating the gene's origin or its function, for example. Some attributes may be associated with more than one project. The project orientation of the present invention permits data analysis and manipulation on the basis of a project categorization.

In a preferred embodiment, the user interface facilitates project data analysis at three levels: a project level, a project sequence level, and a BLAST search level. This allow users to drill down from a high level description of the project, to the actual sequence(s) associated with project (single sequence in the case of EST database), and finally to BLAST against public database.

Suitable interface screens for handling this three level drilling are depicted in FIGS. 5A–5D. In FIG. 5A, a Project Information Query screen 324 is shown. This screen may be reached by a user selecting the project information line of query (button 306) from the main menu screen 302, depicted in FIG. 4. The Project Information Query screen 324 includes a menu button 326 which allows the user to select the type of search query to input. As shown in FIG. 5A, menu 326 is set to "ProjectID." While in this mode, the user is expected to enter one or more ProjectIDs in a field 328. Thereafter, if the user selects a "Search" button the system will return a Project Information Results screen as depicted in FIG. 5B listing information about the entered project (e.g., the project's status, representative sequence, hit description, etc.).

Alternatively, menu button 326 may be selected to allow a choice of "CloneID," "Hit_ID," or "Hit_Description" for example. If the user chooses CloneID, the system expects him or her to enter a desired CloneID in field 328. Each clone in the database has a unique CloneID associated therewith. Upon selection of the Search button 334, the system returns a list of projects with which the selected clone is associated (i.e., projects employing the clone as the birth clone, a member an assemblage, or a member of a cluster). This information may be displayed in a Project Information Results Screen as depicted in FIG. 5B.

Similarly, if the user chooses a Hit_ID or Hit_Description format from menu button 326, he or she will enter an appropriate ID or description in field 328. Upon selection of Search button 334, the system returns a Results screen listing projects containing sequences (as assemblages or clusters for example) that possess the chosen Hit_ID or Hit_Description.

Note that Project Information Query screen 324 includes a "Clear" button allowing users to clear a previous query from field 328. Other features of screen 324 include a "Full-Length" button 332, a "5'Complete" button 330, and a "Secreted" button 331. Selecting button 332 presents a list of projects whose status is "Full-Length" in a Project Information Results Screen. Similarly, selecting button 330 presents a list of projects whose status is "5' Complete" in a Project Information Results Screen. Selecting button 331 presents a list of projects whose category is "Secreted" (that is, projects whose proteins are secreted from the cells in which they are manufactured) in a Project Information Results screen. Of course, other such buttons may be provided to allow a user to directly access specific information in the database. Finally, Query screen 324 includes a row of buttons 338 allowing the user to directly transition to a query page for any of the subjects available through the main menu (e.g., project information, protein function, Northerns, sequence database, and expression). In addition, the user can return to the main menu by selecting a "Main Menu" button from row of buttons 338. Further, the user can receive on line help by selecting a "Help" button from row 338.

FIG. 5B presents a "Project Information Results" screen 340 which returns after a search is executed with Project Information Query screen 324. As mentioned, this screen presents information about each Project identified in the search from screen 324. Thus, this screen presents "first level" information (i.e., project information) in the drilling process mentioned above. Specific presented information may include, in a record 342, a ProjectID, a project Status, a Representative SequenceID, a Hit_ID, a Hit_Description, a Source (i.e., the external database in which the hit occurred), a BLAST score for the hit, and a P-Value for the hit. The last five columns present information based upon the representative sequence of the project. For example, if the project contains a 5' complete sequence as its representative sequence, then the Hit_ID, Hit_Description, Source, BLAST score, and P-Value will all be based upon a hit of that 5' complete sequence against an external database.

Some of the information in record 342 is linked (e.g., via an HTML link) to other information in the database. Such information is indicated by underlining on the pertinent value. Of particular relevance to the three-tiered approach described here is a link from the ProjectID value. If a user selects this value, by double clicking on it for example, the system returns a Sequence Information Results screen such as screen 344 shown in FIG. 5C. This screen includes a list 346 of all sequences within the selected project. Thus, this screen presents the second level information which the user may review to evaluate the project's assembly for example. Note that all entries in the "ProjectID" column have the same value.

Other attributes of the records in list 346 include an assembly checkbox to select sequences for assembly, a SequenceID, a Sequence Type (within the project), a ProjectID, a Hit_ID, a Hit_Description, a Source, a BLAST Score, and a P-Value. Some of these fields provide links as in Project Information Results screen 340.

The SequenceID field provides such a link. By selecting a specific SequenceID, the user may enter the third tier of the analysis. Specifically, in a preferred embodiment, a Sequence Retrieval Results screen 348 such as shown in FIG. 5D is displayed. This screen displays the sequence itself in a sequence field 350. In addition, information about the sequence is provided above the actual sequence in a row 352. The user can conduct BLAST searches of the sequence against external databases by using search buttons 354.

FIG. 5E presents a process flow 400 for the preferred Project Information user interface of this invention, described above. Those of skill in the art will recognize that other process flows are possible without departing from the spirit and scope of the present invention. The process begins at 402 and in a step 404 the system receives a selection of a particular search query category. As previously noted, this embodiment has two basic types of query categories: 1) a project identifier (e.g., "ProjectID" attribute), which returns information about the entered project, and 2) a project member identifier (e.g., "CloneID," "Hit_ID," or "Hit_Description" attributes), which returns a list of projects to which the entered attribute belongs.

At step 406a, the system determines whether the user has selected a project identifier query category. If so, a search query field in the user interface (e.g., field 328 in FIG. 5A) is ready to receive a project search query. Typically, a user will enter one or more ProjectIDs in the search query field 328. Once the search query has been received at step 408a, the system determines, at a decision step 410a, whether the user has selected a search button in the user interface (or otherwise initiated a search). When the search button has been selected, at step 412a the system returns designated attributes from a data record corresponding to the entered project search query. The result is obtained by executing a select statement which includes joining the "FL_Sequences" and "FL_Project" tables of the database on the SequenceID attribute, and the "FL_Project" and "FL_Project_AKA" tables on the ProjectID attribute. The select statement will also include a clause designating those fields or attributes to be returned, some or all of which may be displayed in the Project Information Results screen. An example of a project query search result is shown in the Project Information Results screen depicted in FIG. 5B. Displayed attributes include the entered project's ProjectID, its status, its representative sequence, its Hit_ID, its Hit_Description, its source, its BLAST Score and its P-Value. It should be noted that if the ProjectID returned in this embodiment is different from the queried ProjectID, it is an indication that the queried ProjectID has been merged into the project corresponding to the returned ProjectID (See Section 2, above).

Alternatively, if the system determines at step 406a that the user has not selected a project identifier query category, the system then determines at step 406b whether the user has selected a project member attribute identifier query category. If so, a search query field in the user interface is ready to receive a project member identifier search query. Typically, a user will enter one of a number of project member identifiers, (e.g., "CloneID") in the search query field 328. Once the search query has been received at step 408b, the system determines, at a decision step 410b, whether the user has selected a search button in the user interface (or otherwise initiated a search). When the search button has been selected, the system returns a list of projects (together with associated information) associated with the entered search query at step 412b.

Typical project member attribute identifiers in a preferred embodiment, and there select statements, include the following:

CloneID: Returns information corresponding to the project(s) with which the clone is associated. The result is obtained by executing a select statement which includes joining the "FL_Sequences" and "FL_ProjAllSeq" tables in the database on the SequenceID attribute and the "FL_ProjAllSeq" table to the "FL_Project" table on the ProjectID attribute as a first subquery to identify the projects associated with the queried clone. Then, the "FL_Project" and "FL_Sequences" tables are joined on the SequenceID attribute in a second subquery to return the desired information. A where clause in the select statement is generally matched against the criteria that the user has input in the query for determination of the information to be returned and displayed.

Hit_Description: Returns information about projects that have sequences with that word or phrase in their Hit_Description. The result is obtained by joining the "FL_PFExternalHit" and "FL_Sequences" tables on the Hit_ID and Hit_Type attributes and the "FL_Sequences" and "FL_ProjAllSeq" tables on the SequenceID attribute as a first subquery; and the "FL_Project" and "FL_Sequences" tables on the SequenceID attribute as a second subquery.

Hit_ID: Returns information about the project(s) with which the Hit_ID is associated. The result is obtained by joining the "FL_Sequences" and "FL_ProjAllSeq" tables in the database on the SequenceID attribute and the "FL_ProjAllSeq" table to the "FL_Project" table on the ProjectID attribute as a first subquery; and the "FL_Project" and "FL_Sequences" tables on the SequenceID attribute in a second subquery. The Hit_ID query may also return information about projects having sequences that may have clustered with sequences from other databases which may share the same or a similar Hit_ID.

As previously noted, the Project Information Query screen 324 may include other features. Examples depicted in FIG. 5A include a "Full-Length" button 332, a "5' Complete" button 330, and a "Secreted" button 331. The results returned by these screen have been previously described. The results for each of these buttons are obtained by using select statements reciting the same joins as with the ProjectID query noted above, with where clauses to match the information to be returned against the user's input criteria. This feature is depicted at step 406c in the flow of FIG. 5E.

It should be noted that the system allows the user to exit from the project information query mode at any time. The user may take this route by exiting the program or selecting a screen unrelated to the project information query from among the various buttons 338 provided. This option is depicted at a decision step 414 where the system determines whether the user has selected a link to another screen or exited the program. For purposes of illustration, this step is performed after decision steps 406a and 406b are answered in the negative. Process control is shown returning to decision step 404 when step 414 is answered in the negative. If decision step 414 is answered in the affirmative (i.e., the user elected to leave the project information query mode), the system displays the linked screen if necessary at a step 416.

The loop including steps 406b, 414, and 404 is provided primarily for purposes of illustration. It should be understood that the invention is not limited to this arrangement (or any polling procedure) and may merely await receipt of an appropriate event from the user interface, for example. Moreover, this step could equally well have been depicted anywhere in the flow of process 400.

It should also be noted that various links (preferably HTML links) to additional related screens may also be provided in addition to the buttons 338, such as those illustrated in record 342 of FIG. 5B (Project Information Results screen). As noted above, a user may select a Hypertext link (e.g., a highlighted entry) in order to access linked information in the database. In one embodiment, the following Hypertext links, with their associated linked information, are provided: ProjectID, displays a Sequence Information Results screen listing all sequences in the project, optionally including sequences from other databases that clustered with the project; RepSeqID, displays Electronic Northern results for the project to which the representative sequence belongs; Hit_ID, displays an external database interface page (e.g., Entrez for GenBank; Expasy for Swiss Prot) with information relating to that project; Hit_Description, displays the functional categories under which the project is classified; and Score, displays the BLAST alignment for the project's representative sequence versus its naming GI.

Following the return of query results in step 412b decision step 418 determines whether a user has selected a project from the results list for further analysis (second tier of information). If so, the data corresponding to the selected project is returned at step 412a. Otherwise, following the return of query results in steps 412a or 412b or the display of another selected screen in step 416, the process is then completed at 420.

8. The Northerns User Interface

Another feature of the present invention accessible from the Main Menu screen 302 (FIG. 4) in a preferred embodiment is Electronic Northerns. An Electronic Northern is an electronic analog of a laboratory experiment called a Northern Blot. Like its biological counterpart, an Electronic Northern generally has two principal objectives: 1) to determine the libraries in which a given gene is expressed, and 2) to determine the gene's abundance levels in each of the identified libraries. A preferred embodiment of the user interface for the Northerns feature of the invention will be described below with reference to a process flow, illustrated in FIG. 6A, and selected screen shots, depicted in FIGS. 6B and 6C.

FIG. 6A presents a process flow 500 for the preferred Northerns user interface of this invention. Those of skill in the art will recognize that other process flows are possible without departing from the spirit and scope of the present invention. To perform a Northern analysis, a user selects button 308 in the Main Menu screen 302, which returns the Electronic Northern Query screen 550, illustrated in FIG. 6B. The Northerns process flow 500 begins at 502 and in a step 504 the system receives a selection of a particular search query category. Typically, a user will select a category from a pull-down menu which is displayed when the user clicks on the search query category box 552. At step 506, the system determines whether the user has selected a search query category. If so, a search query text box 554 in the user interface is ready to receive a Northern search query. Typically, a user will enter a search query associated with the search query category selected in box 552 in the search query text box 554.

For example, a Northern analysis may be conducted on the basis of ProjectID by selecting that category from the pull-down menu in box 552. A user may then enter a ProjectID number in the search query text box 554. In a preferred embodiment, the search is conducted using the representative sequence corresponding to the entered ProjectID. In this preferred embodiment, the select statement for this search includes joining the "FL_NorthernAbun" table to the "Library" table of Incyte Pharmaceuticals, Inc.'s LifeSeq™ database on the LibraryID attribute and the "FL_NorthernAbun" table to the "FL_Project" table on the ProjectID attribute.

Alternatively, the search may be conducted on the basis of a CloneID by selecting that search query type and entering a clone number in text box 554. In a preferred embodiment, the select statement for this search has a first subquery joining the "FL_ProjAllSeq" table to the "FL_Sequences" table on the SequenceID attribute. The second subquery is the same as the join used for the ProjectID Northern query, noted above.

Once the search query has been received at step 508, the system determines, at a decision step 510, whether the user has selected a search button in the user interface (or otherwise initiated a search). When the search button has been selected, at step 512 the system returns a list of all libraries which contain members of the project with which the search query is associated. Preferably, the results are provided in order of decreasing abundance of project members in each of the identified libraries.

In a preferred embodiment, a Northern analysis seeks matches to a representative sequence of a project in a database of the present invention (i.e., full-length project-based database) following determination of the full-length sequence of the project's associated gene. Once the representative sequence is identified, it is compared against sequence data in another database (e.g., Incyte Pharmaceuticals, Inc.'s LifeSeq™ database). Those libraries having clones with sequences matching a representative sequence with a Percent Identity equal to or greater than 90 and having a minimum BLAST Score of 250 are returned in an. Electronic Northern results screen. In alternative embodiments, the Northern analysis may be extended to additional internal or external databases, to non-fulllength status projects, may be based on other project member attributes, and may also consider cluster information for the identified clone matches. Moreover, the stringency of the matching may be varied.

An example of an Electronic Northern search result screen 560 is shown in FIG. 6C. The returned results are for the search query ProjectID 9118, which is identified in text line 562. The results identify the libraries in which a match to the representative sequence of ProjectID 9118 was found ("Library" field 564), and provide a description of the libraries' sources ("Lib Description" field 566). In addition, the abundance (number of members (clones) of a project in a library or libraries; "Abun" field 568) and percent abundance (the abundance divided by the total number of sequences in a library or libraries; "Pct Abun" field 570) of clones matching the representative sequence in each library is noted.

As in the other features of the present database, the system allows the user to exit from the Electronic Northern query mode at any time. The user may take this route by exiting the program or selecting a screen unrelated to the Electronic Northern query from among the various buttons 555 provided in both the Query 550 and Results 560 screens. This option is depicted at a decision step 514 where the system determines whether the user has selected a link to another screen or exited the program. For purposes of illustration, this step is performed after decision step 510 is answered in the negative. Process control is shown returning to decision step 508 when step 514 is answered in the negative. If decision step 514 is answered in the affirmative (i.e., the user elected to leave the Electronic Northern query mode), the system displays the linked screen if necessary at a step 516.

The loop including steps 510, 508 and 514 is provided primarily for purposes of illustration. It should be understood that the invention is not limited to this arrangement (or any polling procedure) and may merely await receipt of an appropriate event from the user interface, for example. Moreover, this step could equally well have been depicted anywhere in the flow of process 500.

It should also be noted that various links (preferably HTML links) to additional related screens may also be provided in addition to the buttons 555, such as those illustrated in result line 580 of FIG. 6C (Electronic Northern Results screen). This feature is depicted at a decision step 518 where the system determines whether the user has selected a Hypertext link to another screen. This step is performed following the display of the search results in the Electronic Northern Results screen at step 512. A user may select (e.g., by clicking) a Hypertext link (e.g., one indicated by underlining or highlighting) in order to access linked information in the database. If decision step 518 is answered in the affirmative (i.e., the user selected a Hypertext link), the system displays the linked screen at a step 520.

In the embodiment illustrated in FIG. 6C, a user may select a Library link in order to have a more complete description for the selected library returned. The Library link returns the Library Information Results screen from Incyte Pharmaceuticals, Inc.'s LifeSeq™ database. The user may also select the Abun field for listed library to have detailed information about the clone(s) associated with the particular project returned. For example, FIG. 6D illustrates the result of a user selecting the Abun field (clicking on the "7") in result line 580 in screen 560. Clone Information Results screen 590 displays information relating to the seven clones matched to the representative sequence of project 9118 found in Library HNT2RAT01. In this embodiment, the result includes the ClusterID, CloneID, Library, Hit_ID, Hit_Description and other attributes of each clone in the Library. This screen may be from the database to which the displayed clones belong.

Following the return of query results or the selection of another screen, the process is then completed at 522.

9. The Expression User Interface

The present invention also may also provide a feature which allows a user to view projects in the database that have been categorized under specific expression profiles. Such categories include secreted, induced expression, and various tissue-specific categories. In contrast with the protein function categories noted above, each project will generally have a single designated expression category based on its tissue or system of origin, or on corresponding annotations in other databases.

In a preferred embodiment, the Expression feature is accessible from the Main Menu screen 302 (FIG. 4). When a user selects button 310 in the Main Menu screen 302, Expression Query screen 625 (FIG. 7B) is returned. FIG. 7A presents a process flow 600 for the preferred Expression user interface of this invention. Those of skill in the art will recognize that other process flows are possible without departing from the spirit and scope of the present invention. The Expression process flow 600 begins at 602 and in a step 604 the system receives a user's selection of one or more expression categories from the scrolling list 630 provided in query screen 625, or from the checkbox 632 provided in screen 625 to allow a user to easily select all expression categories for the query.

Once the search query has been selected at step 604, the system determines, at a decision step 605, whether the user has selected a search button in the user interface (or otherwise initiated a search). When the search button 634 has been selected, the results are returned at step 606 in the Expression Results screen 650, illustrated in FIG. 7B. The result is obtained by executing a select statement which includes joining the "FL_Sequences" and "FL_Project" tables of the database on the SequenceID attribute. The results list those projects in the database which are in the queried expression category(ies). The list identifies each project's representative sequence, includes the expression category and Hit_Description for each project's representative sequence and presents status information for each project.

The Expression Results screen preferably includes various HTML links to additional related screens in the results entries in screen 650. As shown in FIG. 7B, the entries in the ProjectID 652 and Hit_Description 654 fields in the results are underlined indicating that they are Hypertext links to additional screens. In a preferred embodiment, selecting a ProjectID link will display a Sequence Information Results screen (not shown) showing SequenceIDs associated with that project, optionally including associated clustered sequences. A user may move from this second level of analysis to a third level by selecting a SequenceID link to return a Sequence Retrieval results screen from which sequence alignment searches may be performed. Alternatively, Selecting a Hit_Description link in the Expression Results screen 650 will display the functional categories under which the project is classified (See patent application Ser. No. 08/812,290 (attorney docket no ICYTP005), previously incorporated by reference). This is depicted in FIG. 7A by decision step 608 and display step 610, and decision step 612 and display step 614, respectively.

As with the previously described features of the database, the Expression Results screen 650 also has buttons 656 which allow a user to exit from the Expression mode at any time. This option is not depicted in process flow 600, but could be shown anywhere in the process flow as a loop providing the option to exit the program or display an unrelated screen.

Following the return of query results or the selection of another screen, the process is then completed at 616.

10. Conclusion

Although a few specific embodiments of the present invention have been described in detail, it should be understood that the present invention may be embodied in many other specific forms without departing from the spirit or scope of the invention as recited in the claims. For example, while the gene expression databases of this invention have been described as storing nucleic acid sequences grouped as projects (including birth clones, long read sequences, full-length sequences, etc. originating from mRNA), there is in principle no reason why other sequence units cannot also be employed. For example, the databases of this invention could be employed to store genomic DNA sequences. Moreover, the various screen shots and process flows described are only representative of the features of preferred embodiments the present invention and do not limit its scope which is defined by the appended claims.

What is claimed is:

1. A computer system comprising:
    a database having sequence records containing information identifying one or more projects to which each of said sequence records belong, each of said projects grouping one or more biomolecular sequences generated during work to obtain a full-length gene sequence from a shorter sequence; and
    a user interface allowing a user to selectively view information regarding said one or more projects.

2. The computer system of claim 1, wherein the biomolecular sequences include nucleic acids.

3. The computer system of claim 2, wherein the biomolecular sequences are selected from the group consisting of first pass sequences, assemblages, 5' complete sequences, full-length sequences, and combinations thereof.

4. The computer system of claim 1, wherein the biomolecular sequences include amino acids.

5. The computer system of claim 1, wherein the records include descriptive information from an external database, which information correlates said biomolecular sequences to records in said external database.

6. The computer system of claim 5, wherein the external database is GenBank.

7. The computer system of claim 1, wherein said user interface allows users to view at least three levels of project information, which levels include a project information results level listing at least some of said one or more projects in said database, a sequence information results level listing at least some of said sequences associated with a given project, and a sequence retrieval results level sequentially listing monomers which comprise a given sequence.

8. The computer system of claim 1, wherein said user interface further comprises links which a user may select to access additional information.

9. The computer system of claim 8, wherein said links comprise HTML links.

10. A method of using a computer system to present information pertaining to a plurality of sequence records stored in a database, said sequence records containing information identifying one or more projects to which each of said sequence records belong, each of said projects grouping one or more biomolecular sequences generated during work to obtain a full-length gene sequence from a shorter sequence, the method comprising:

providing an interface for entering query information relating to one or more of said projects;

locating data corresponding to said entered query information; and displaying the data corresponding to said entered query information.

11. The method of claim 10, wherein said biomolecular sequences include nucleic acid sequence, amino acid sequences, or both nucleic acid sequences and amino acid sequences.

12. The method of claim 10, wherein said query information identifies one or more project identifier attributes, and said corresponding data identifies one or more project member attributes.

13. The method of claim 12, wherein said one or more project member attributes contain information relating to project status, project representative sequence and matches of project member sequences to external databases.

14. The method of claim 10, wherein said query information identifies one or more project member attributes, and said corresponding data identifies one or more project identifier attributes.

15. The method of claim 14, wherein said one or more project member attributes contain information relating to clones or matches of project member to external database sequences or annotations.

16. A method of using a computer system to present information pertaining to a plurality of sequence records stored in a database, said sequence records containing information identifying one or more projects to which each of said sequence records belong, each of said projects grouping one or more biomolecular sequences generated during work to obtain a full-length gene sequence from a shorter sequence, the method comprising:

displaying a list of one or more project identifiers;

determining which project identifier or identifiers from said list is selected by a user;

displaying a second list of one or more biomolecular sequence identifiers associated with the selected project identifier or identifiers;

determining which sequence identifier or identifiers from said second list has been selected by a user; and displaying a third list of one or more sequences corresponding to the selected sequence identifier or identifiers.

17. The method of claim 16, further comprising:

determining which sequence from said third list has been selected by a user;

initiating a sequence alignment search of the selected sequence against other databased sequences; and displaying the results of the alignment search.

18. A computer program product comprising a computer-usable medium having computer-readable program code embodied thereon relating to a plurality of sequence records stored in a database, said sequence records containing information identifying one or more projects to which each of said sequence records belong, each of said projects grouping one or more biomolecular sequences generated during work to obtain a full-length gene sequence from a shorter sequence, the computer program product comprising computer-readable program code for effecting the following steps within a computing system:

providing an interface for entering query information relating to one or more of said projects;

locating data corresponding to said entered query information; and displaying the data corresponding to said entered query information.

19. The computer program product of claim 18, wherein said query information identifies one or more project attributes, and said corresponding data identifies one or more project member attributes.

20. The computer program product of claim 18, wherein said query information identifies one or more project member attributes, and said corresponding data identifies one or more project attributes.

21. A computer system comprising:

a database having sequence records containing information identifying one or more projects to which each of said sequence records belong, each of said projects grouping one or more biomolecular sequences generated during work to obtain a full-length gene sequence from a shorter sequence; and a user interface capable of allowing a user to select one or more project identifiers or project member identifiers specifying one or more sequences to be compared with one or more cDNA sequence libraries, and displaying matches resulting from said comparison.

22. The computer system of claim 21, wherein selection of a project identifier specifies a representative sequence of said project for the comparison.

23. The computer system of claim 21, wherein the one or more project member identifiers is a CloneID attribute, and wherein selection of said CloneID attribute specifies one or more representative sequences of one or more projects associated with said CloneID attribute for the comparison.

24. The computer system of claim 21, wherein the biomolecular sequences include nucleic acids.

25. The computer system of claim 21, wherein said one or more cDNA sequence libraries are contained within the project database.

26. The computer system of claim 21, wherein said one or more cDNA sequence libraries include libraries not contained within the project database.

27. The computer system of claim 21, wherein said user interface is further capable of:

determining whether a user has selected a link to additional information relating to said matches; and displaying the additional information associated with any selected link.

28. The computer system of claim 27, wherein said additional information comprises abundance and percent abundance figures for said matches.

29. A method of using a computer system to present comparative information pertaining to a plurality of sequence records stored in a database, said sequence records containing information identifying one or more projects to which each of said sequence records belong, each of said projects grouping one or more biomolecular sequences generated during work to obtain a full-length gene sequence from a shorter sequence, the method comprising:

providing an interface capable of allowing a user to select one or more project identifiers or project member identifiers specifying one or more sequences;

comparing said one or more specified sequences with one or more cDNA sequence libraries; and displaying matches resulting from said comparison.

30. The method of claim 29, wherein said one or more project identifiers or project member identifiers is a ProjectID attribute, and said ProjectID attribute specifies a representative sequence of said project for the comparison.

31. The method of claim 29, wherein the one or more project identifiers or project member identifiers is a CloneID attribute, and wherein selection of said CloneID attribute specifies one or more representative sequences of one or more projects associated with said CloneID attribute for the comparison.

32. The method of claim 29, wherein the biomolecular sequences include nucleic acids.

33. The method of claim 29, wherein said one or more cDNA sequence libraries are contained within the project database.

34. The method of claim 29, wherein said one or more cDNA sequence libraries include libraries not contained within the project database.

35. The method of claim 29, further comprising:

determining whether a user has selected a link to additional information relating to said matches; and displaying the additional information associated with any selected link.

36. The method of claim 35, wherein said additional information comprises abundance and percent abundance figures for said matches.

37. A computer system comprising:

a database having sequence records containing information identifying one or more projects to which each of said sequence records belong, each of said projects grouping one or more biomolecular sequences generated during work to obtain a full-length gene sequence from a shorter sequence; and a user interface allowing a user to view expression information pertaining to said projects by selecting one or more expression categories for a query, and displaying the result of said query.

38. The computer system of claim 37, wherein the biomolecular sequences include nucleic acids.

39. The computer system of claim 38, wherein the biomolecular sequences are selected from the group consisting of first pass sequences, assemblages, 5' complete sequences, full-length sequences, and combinations thereof.

40. The computer system of claim 37, wherein said expression categories include induced expression, regulated expression, secreted, splice variant, and one or more tissue specific categories.

41. The computer system of claim 40, wherein said tissue specific categories include cardiovascular, dermatologic, developmental, endocrine, gastrointestinal, hematologic, hepatic, musculoskeletal, nervous, pancreas, reproductive—female, reproductive—male, respiratory and urologic.

42. The computer system of claim 37, wherein said user interface includes a pull-down menu for selection of said one or more expression categories.

43. The computer system of claim 37, wherein said user interface includes a checkbox for selection of all of said expression categories.

44. The computer system of claim 37, wherein said user interface further comprises links which a user may select to access additional information relating to said expression categories.

45. The computer system of claim 37, wherein said links comprise HTML links.

46. A method of using a computer system to view expression information pertaining to one or more projects, each of said projects grouping one or more biomolecular sequences generated during work to obtain a full-length gene sequence from a shorter sequence, said computer system comprising a database storing a plurality of sequence records, said sequence records containing information identifying one or more projects to which each of said sequence records belong, the method comprising:

providing an interface which allows a user to select one or more expression categories as a query;

locating projects belonging to the selected one or more expression categories; and displaying a list of located projects.

47. The method of claim 46, wherein said expression categories include induced expression, regulated expression, secreted, splice variant, and one or more tissue specific categories.

48. The method of claim 46, wherein said tissue specific categories include cardiovascular, dermatologic, developmental, endocrine, gastrointestinal, hematologic, hepatic, musculoskeletal, nervous, pancreas, reproductive—female, reproductive—male, respiratory and urologic.

49. The method of claim 46, wherein said user interface includes a pull-down menu for selection of said one or more expression categories.

50. The method of claim 46, further comprising:

determining whether a user has selected a link to additional information relating to said expression categories; and displaying the additional information associated with any selected link.

51. A computer system comprising:

a database having sequence records containing information identifying one or more projects to which each of said sequence records belong, each of said projects grouping one or more biomolecular sequences generated during work to obtain a full-length gene sequence from a shorter sequence; and a user interface allowing a user to selectively view information regarding said one or more projects;

wherein said user interface displays information to a user in a format common to one or more other sequence databases.

52. The computer system of claim 51 wherein said other sequence databases are selected from the group including general purpose short sequence databases, microbial genomic sequence database, and plant sequence databases.

* * * * *